(12) United States Patent
Zimmerman et al.

(10) Patent No.: US 9,869,339 B2
(45) Date of Patent: Jan. 16, 2018

(54) END-EFFECTOR JAW CLOSURE TRANSMISSION SYSTEMS FOR REMOTE ACCESS TOOLS

(71) Applicant: FlexDex, Inc., Brighton, MI (US)

(72) Inventors: Zachary Zimmerman, Waterford, MI (US); Shorya Awtar, Ann Arbor, MI (US); Bruce Johnson, Elkins, NH (US); Christopher K. Holmes, Harvard, MA (US); Peter F. Costa, Winthrop, MA (US); Ryan Brook Rank, Ann Arbor, MI (US)

(73) Assignee: FlexDex, Inc., Brighton, MI (US)

( * ) Notice: Subject to any disclaimer, the term of this patent is extended or adjusted under 35 U.S.C. 154(b) by 0 days.

(21) Appl. No.: 15/286,547

(22) Filed: Oct. 5, 2016

(65) Prior Publication Data

US 2017/0097035 A1 Apr. 6, 2017

Related U.S. Application Data

(60) Provisional application No. 62/237,476, filed on Oct. 5, 2015, provisional application No. 62/237,483, filed on Oct. 5, 2015.

(51) Int. Cl.
*F16C 1/12* (2006.01)
*F16H 21/44* (2006.01)
(Continued)

(52) U.S. Cl.
CPC .......... *F16C 1/12* (2013.01); *A61B 17/00234* (2013.01); *A61B 17/2909* (2013.01);
(Continued)

(58) Field of Classification Search
CPC . F16C 1/12; A61B 90/50; A61B 90/53; A61B 2090/508; A61B 17/00234; A61B 17/2812; A61B 17/282; A61B 2017/00323; A61B 2017/00327; A61B 2017/0042; A61B 2017/2837; A61B 2017/2841; A61B 2017/2912; A61B 2017/2913; A61B 2017/2915; A61B 2017/2919; A61B 2017/2925; A61B 2017/2932;
(Continued)

(56) References Cited

U.S. PATENT DOCUMENTS

| 3,497,083 A | 2/1970 | Anderson et al, |
| 4,328,839 A | 5/1982 | Lyons et al. |

(Continued)

FOREIGN PATENT DOCUMENTS

| GB | 0937587 A | 10/1964 |
| GB | 973587 A | 10/1964 |

(Continued)

OTHER PUBLICATIONS

Awtar et al.; A minimally invasive surgical tool with enhanced dexterity and intuitive actuation; J. Med. Devices; 4(3); 8 pages; (Author's Draft; 12 pages); Sep. 10, 2010.

(Continued)

*Primary Examiner* — Jocelin Tanner
(74) *Attorney, Agent, or Firm* — Shay Glenn LLP

(57) ABSTRACT

A jaw closure transmission system is presented comprising an input sub-system, output sub-system and a transmission sub-system.

17 Claims, 17 Drawing Sheets

(51) Int. Cl.
*A61B 17/00* (2006.01)
*A61B 17/29* (2006.01)
*A61B 34/00* (2016.01)

(52) U.S. Cl.
CPC ............ *A61B 34/71* (2016.02); *F16H 21/44* (2013.01); *A61B 2017/0042* (2013.01); *A61B 2017/00314* (2013.01); *A61B 2017/00442* (2013.01); *A61B 2017/2932* (2013.01); *A61B 2017/2937* (2013.01); *A61B 2034/715* (2016.02)

(58) Field of Classification Search
CPC .... A61B 2017/2933; A61B 2017/2934; A61B 2017/2946; A61B 34/71; A61B 2034/715; A61B 17/2909; A61B 2017/2937; A61B 2017/00442; A61B 2017/00314; F16H 21/44
See application file for complete search history.

(56) References Cited

U.S. PATENT DOCUMENTS

| | | |
|---|---|---|
| 4,466,649 A | 8/1984 | Ozawa |
| 4,568,311 A | 2/1986 | Miyake |
| 4,712,545 A | 12/1987 | Honkanen |
| 4,750,475 A | 6/1988 | Yoshihashi |
| 4,754,909 A | 7/1988 | Barker et al. |
| 4,950,273 A | 8/1990 | Briggs |
| 5,021,969 A | 6/1991 | Okamura et al. |
| 5,069,596 A | 12/1991 | Mueller et al. |
| 5,147,357 A * | 9/1992 | Rose ...................... A61B 17/29 606/49 |
| 5,209,747 A | 5/1993 | Knoepfler |
| 5,297,443 A | 3/1994 | Wentz |
| 5,317,952 A | 6/1994 | Immega |
| 5,323,570 A | 6/1994 | Kuhlman et al. |
| 5,330,502 A | 7/1994 | Hassler et al. |
| 5,350,391 A | 9/1994 | Iacovelli |
| 5,368,600 A | 11/1994 | Failla et al. |
| 5,374,277 A | 12/1994 | Hassler |
| 5,454,827 A | 10/1995 | Aust et al. |
| 5,456,695 A | 10/1995 | Herve Dallemagne |
| 5,549,637 A | 8/1996 | Crainich |
| 5,599,151 A | 2/1997 | Daum et al. |
| 5,620,415 A * | 4/1997 | Lucey ................ A61B 17/1608 604/22 |
| 5,626,608 A | 5/1997 | Cuny et al. |
| 5,683,412 A * | 11/1997 | Scarfone ................ A61B 17/29 606/205 |
| 5,713,505 A | 2/1998 | Huitema |
| 5,716,352 A | 2/1998 | Viola et al. |
| 5,735,874 A | 4/1998 | Measamer et al. |
| 5,782,748 A | 7/1998 | Palmer et al. |
| 5,807,376 A | 9/1998 | Viola et al. |
| 5,817,084 A | 10/1998 | Jensen |
| 5,820,009 A | 10/1998 | Melling et al. |
| 5,853,412 A * | 12/1998 | Mayenberger ..... A61B 18/1445 606/207 |
| 5,860,995 A | 1/1999 | Berkelaar |
| 5,908,436 A | 6/1999 | Cuschieri et al. |
| 6,088,020 A | 7/2000 | Morley et al. |
| 6,270,453 B1 | 8/2001 | Sakai |
| 6,309,403 B1 | 10/2001 | Minor et al. |
| 6,312,435 B1 | 11/2001 | Wallace et al. |
| 6,330,837 B1 | 12/2001 | Charles et al. |
| 6,714,839 B2 | 3/2004 | Salisbury et al. |
| 6,853,879 B2 | 2/2005 | Sunaoshi |
| 6,889,116 B2 | 5/2005 | Jinno |
| 6,994,716 B2 | 2/2006 | Jinno et al. |
| 7,101,363 B2 | 9/2006 | Nishizawa et al. |
| 7,147,650 B2 | 12/2006 | Lee |
| 7,553,275 B2 | 6/2009 | Padget et al. |
| 7,608,083 B2 | 10/2009 | Lee et al. |
| 7,708,756 B2 | 5/2010 | Nobis et al. |
| 7,736,254 B2 | 6/2010 | Schena |
| 8,029,531 B2 | 10/2011 | Lee et al. |
| 8,425,408 B2 | 4/2013 | Boulais et al. |
| 8,465,475 B2 | 6/2013 | Isbell |
| 8,528,440 B2 | 9/2013 | Morley et al. |
| 8,540,748 B2 | 9/2013 | Murphy et al. |
| 8,551,076 B2 | 10/2013 | Duval et al. |
| 8,603,135 B2 | 12/2013 | Mueller |
| 8,668,702 B2 | 3/2014 | Awtar et al. |
| 8,672,206 B2 | 3/2014 | Aranyi et al. |
| 8,764,448 B2 | 7/2014 | Yang et al. |
| 8,992,422 B2 | 3/2015 | Spivey et al. |
| 9,161,771 B2 | 10/2015 | Steger |
| 9,220,398 B2 | 12/2015 | Woodley et al. |
| 9,696,700 B2 | 7/2017 | Beira et al. |
| 2001/0031983 A1 | 10/2001 | Brock et al. |
| 2003/0036748 A1 | 2/2003 | Cooper et al. |
| 2003/0135203 A1 | 7/2003 | Wang et al. |
| 2003/0176880 A1 * | 9/2003 | Long ..................... A61B 10/04 606/167 |
| 2003/0176948 A1 | 9/2003 | Green |
| 2004/0023616 A1 | 2/2004 | Straub et al. |
| 2004/0138700 A1 | 7/2004 | Cooper et al. |
| 2004/0236316 A1 | 11/2004 | Danitz et al. |
| 2004/0253079 A1 | 12/2004 | Sanchez |
| 2005/0004431 A1 | 1/2005 | Kogasaka et al. |
| 2005/0038469 A1 | 2/2005 | Lang |
| 2005/0107667 A1 | 5/2005 | Danitz et al. |
| 2006/0111210 A1 | 5/2006 | Hinman |
| 2006/0111616 A1 | 5/2006 | Danitz |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0078565 A1 | 4/2007 | Ghodoussi et al. |
| 2008/0039256 A1 | 2/2008 | Jinno et al. |
| 2008/0065098 A1 | 3/2008 | Larkin |
| 2008/0177285 A1 | 7/2008 | Brock et al. |
| 2010/0004606 A1 | 1/2010 | Hansen et al. |
| 2010/0016853 A1 | 1/2010 | Burbank |
| 2010/0030018 A1 | 2/2010 | Fortier et al. |
| 2010/0056863 A1 | 3/2010 | Dejima et al. |
| 2010/0234831 A1 | 9/2010 | Hinman et al. |
| 2011/0118707 A1 | 5/2011 | Burbank |
| 2011/0152881 A1 | 6/2011 | Conner et al. |
| 2011/0152922 A1 | 6/2011 | Jeong |
| 2012/0095298 A1 | 4/2012 | Stefanchik et al. |
| 2012/0186383 A1 | 7/2012 | Schvalb et al. |
| 2012/0277762 A1 | 11/2012 | Lathrop et al. |
| 2013/0012958 A1 | 1/2013 | Marczyk et al. |
| 2013/0023868 A1 | 1/2013 | Worrell et al. |
| 2013/0023974 A1 | 1/2013 | Amrani |
| 2013/0066334 A1 | 3/2013 | Schoepp |
| 2013/0172860 A1 | 7/2013 | Szewczyk et al. |
| 2013/0239734 A1 | 9/2013 | Hinman |
| 2014/0135805 A1 | 5/2014 | Windgassen et al. |
| 2014/0142595 A1 | 5/2014 | Awtar et al. |
| 2014/0371532 A1 | 12/2014 | Trovato |
| 2015/0164601 A1 | 6/2015 | Sholev |
| 2015/0230697 A1 | 8/2015 | Phee et al. |
| 2016/0135830 A1 | 5/2016 | Volkmer et al. |
| 2016/0256232 A1 | 9/2016 | Awtar et al. |
| 2016/0291383 A1 | 10/2016 | Han et al. |
| 2016/0303734 A1 | 10/2016 | Bowles et al. |
| 2017/0245954 A1 | 8/2017 | Beira |

FOREIGN PATENT DOCUMENTS

| | | |
|---|---|---|
| JP | 3-292879 A | 12/1991 |
| JP | 8-84702 A | 4/1996 |
| JP | 2002102248 A | 4/2002 |
| JP | 2003061969 A | 3/2003 |
| JP | 2007130485 A | 5/2007 |
| WO | WO2006/036067 A2 | 4/2006 |
| WO | WO2007/146894 A2 | 12/2007 |
| WO | WO2008/020964 A2 | 2/2008 |
| WO | WO2014/033717 A1 | 3/2014 |

(56) References Cited

FOREIGN PATENT DOCUMENTS

| WO | WO2015/125140 A1 | 8/2015 |
|---|---|---|
| WO | WO2016/063213 A1 | 4/2016 |
| WO | WO2016/161449 A1 | 10/2016 |

OTHER PUBLICATIONS

Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Sharma et al.; U.S. Appl. No. 15/284,345 entitled "Handle mechanism providing unlimited roll," filed Oct. 3, 2016.

Licht et al.; U.S. Appl. No. 15/286,489 entitled "Medical devices having smoothly articulating multi-cluster joints," filed Oct. 5, 2016.

Clement et al.; Design of a Snake-Like Manipulator; Robotics and Autonomous Systems; 6(3); pp. 265-282; Jul. 1990.

Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.

Jug et al.; The JPL Serpentine Robot: a 12 DOF System for Inspection (Conference Paper); Proceedings—IEEE International Conference on Robotics and Automation 3: 5 pgs.; Jun. 1995.

Walker et al.; Novel 'Elephant's Trunk' Robot; IEEE/ASME International Conference on Advanced Intelligent Mechatronics, AIM; Piscataway, NJ, United States; pp. 410-415; Sep. 19-23, 1999.

Wikipedia; Constant Velocity Joint; 6 pgs.; retrieved from the internet (https://en.wikipedia.org/wiki/Constant-velocity_joint) on Dec. 22, 2016.

\* cited by examiner

END-EFFECTOR JAW CLOSURE TRANSMISSION SYSTEMS FOR REMOTE ACCESS TOOLS

CROSS REFERENCE TO RELATED APPLICATIONS

This patent application claims priority to U.S. provisional patent application No. 62/237,476, titled "END-EFFECTOR JAW CLOSURE TRANSMISSION SYSTEMS FOR REMOTE ACCESS TOOLS," and filed on Oct. 5, 2015; and to U.S. provisional patent application No. 62/237,483, titled "ARTICULATING JOINT AND SUPPORTING MEMBER THEREOF", filed on Oct. 5, 2015, each of which is herein incorporated by reference in its entirety.

This application may also be related to U.S. patent application Ser. No. 15/130,915, titled "ATTACHMENT APPARATUS FOR REMOTE ACCESS TOOLS", and filed on Apr. 15, 2016, which claimed priority to U.S. Provisional Patent Application No. 62/147,998, filed Apr. 15, 2015 (and titled "FOREARM ATTACHMENT APPARATUS FOR REMOTE ACCESS TOOLS"), and U.S. Provisional Patent Application No. 62/236,805, filed Oct. 2, 2015 (titled "FOREARM ATTACHMENT APPARATUS FOR REMOTE ACCESS TOOLS"). This application may also be related to U.S. patent application Ser. No. 15/054,068, filed on Feb. 25, 2016, and titled "PARALLEL KINEMATIC MECHANISMS WITH DECOUPLED ROTATIONAL MOTIONS" which claims priority as a CIP to U.S. patent application Ser. No. 14/166,503, filed on Jan. 28, 2014, and titled "MINIMAL ACCESS TOOL," Publication No. US-2014-0142595-A1, which is a continuation of U.S. patent application Ser. No. 12/937,523, filed on Apr. 13, 2009, now U.S. Pat. No. 8,668,702, which claimed priority to U.S. provisional patent application No. 61/044,168, filed on Apr. 11, 2008. Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are transmission systems that are used for remote access instruments, for example minimally invasive surgical tools. In particular the apparatus provides a transmission system design that utilizes the transmission member as an energy storing device, over a certain portion of input stroke, to achieve a specific desired performance of the surgical tool. In general, the transmission member may be referred to as a jaw closure transmission member, or as a jaw closure transmission cable, or as a transmission cable, or as a cable or the like.

BACKGROUND

Typically, in laparoscopic, endoscopic, or other minimally invasive surgical procedures, a small incision or puncture is made in a patient's body. A cannula is then inserted into a body cavity through the incision, which provides a passageway for inserting various surgical devices such as scissors, dissectors, retractors or similar instruments. To facilitate operability through the cannula, instruments adapted for laparoscopic surgery typically embody a relatively narrow shaft supporting an end-effector (EE) at its distal end and a lever or handle at its proximal end. Arranging the shaft of such an instrument through the cannula allows a surgeon to manipulate the proximal handle from outside the body to cause the distal end-effector to carry out a surgical procedure at a remote internal surgical site. In most embodiments, the handle and tool shaft can be directly connected and roll rotation of the entire handle may drive rotation of the entire tool shaft and end-effector. Some alternative laparoscopic tools, such as, for example, U.S. Pat. No. 8,668,702 includes a handle that is not directly connected to the tool shaft but connected via an input joint (e.g., comprising a pair of transmission strips) which still allows for roll rotation of the tool shaft and end-effector by way of handle rotation. In general, a handle body may be referred to as a handle reference, or as a palm grip, handle shell, or the like.

A laparoscopic or endoscopic instrument may provide a surgeon with the ability to transfer high force loads from the proximal end of the tool to the distal end. These forces are transferred through the instrument through an input, output and transmission member sub-system, where the sub-system consists of a mechanism, as seen in most surgical instruments, such as U.S. Pat. No. 5,330,502. The input mechanism generally consists of an actuating lever body as an input and an output (for example, a shuttle coupled to the handle body via a one Degree of Freedom (DoF) slider joint). As a user actuates the handle lever, the motion is transferred to the shuttle, and the amount that the shuttle displaces is based on the input mechanism's mechanical advantage, or transmission ratio. The terms transmission ratio and mechanical advantage are both used in this document since the transmission ratio and mechanical advantage are, in general, simply the inverse of each other. When emphasizing force, the attribute mechanical advantage is used, and when emphasizing displacement, the attribute transmission ratio is used. Similarly, the output mechanism can have a varying mechanical advantage, or transmission ratio, over the output stroke. For a mechanical surgical instrument which requires a high force output while not compromising on output displacement, this varying mechanical advantage of both the input mechanism and the output mechanism will have a certain desirable profile. The mechanical advantage at the initial segment of the stroke can be low because no force build up is required initially; however the mechanical advantage at the end of the stroke needs to be high to allow a reasonable force input to be amplified into a large force output. The transmission members used in the prior art are generally stiff in the direction of transmission. However, this transmission member does not have to be rigid. In the transmission systems described herein, the transmission member itself is designed to have a finite stiffness so that it acts as an energy storage member during certain portions of the input stroke of the device. This offers a unique performance of the device and has many benefits over rigid or highly stiff transmission members.

SUMMARY OF THE DISCLOSURE

Described herein are jaw closure transmission systems that provide enhanced closure security and feel. These closure transmissions may be part of any appropriate apparatus, including medical devices (e.g., minimally invasive surgical tools), or any other application in which it is beneficial or desirable to have a jaw closure mechanism that may securely grip and provide feedback to the user on grip strength, as will be described herein.

In general, the jaw closure transmission systems described herein may include rigid and compliant transmission elements, including an input (e.g., a jaw actuation input), an output (e.g., jaw mechanism), a transmission cable having a finite stiffness in a transmission direction, and a rigid or flexible transmission guiding element, wherein the transmission element stores energy during closure transmission to achieve unique and desirable functionality.

The jaw closure transmission systems described herein may include three (or more) sub-systems that are serially connected that take an input, in the form of handle lever displacement and force from the user, and produce an output that presents as moving jaw displacement and clamp load. In general, a moving jaw may be referred as a movable jaw, or as an end-effector moving jaw, or as an may be completely rigid in all directions, such as a frame, EE moving jaw, or the like. The three sub-systems are as follows: (a) input sub-system: handle assembly; (b) output sub-system: jaw assembly; (c) transmission sub-system (e.g., transmission member, e.g., cable, and transmission guide, e.g., flexible conduit). The input sub-system may include the input in a handle assembly that comprises a handle body or shell that serves as the local reference or ground, and a handle lever configured to receive user input in the form of closing or displacing the handle lever relative to the handle body. In general, the full closure displacement of the handle lever with respect to the handle body is referred to as the input stroke. At full closure, i.e., at the end of an input stroke, the handle lever reaches a hard-stop relative to the handle body. At this hard stop, there may be a single locking or latching feature that keeps the handle lever latched closed relative to the handle body. An unlatching/unlocking feature (e.g., a releasable lock) unlocks the handle lever and allows it to open again with respect to the handle body.

The handle assembly may also include a handle output (handle mechanism output) that connects to the transmission cable. The handle output may be a shuttle, a push rod, a pull rod, etc. The output typically interfaces with the transmission member and provides an actuation motion to the proximal end of the transmission member.

In general, the handle mechanism is configured as a mechanical linkage system that translates the closing motion of the handle lever relative to the handle body to a corresponding actuation motion of the handle shuttle relative to the handle body. The handle mechanism provides a transmission ratio and mechanical advantage between the handle lever and the handle shuttle so as to produce the appropriate actuation displacement and force at the proximal end of the transmission member (e.g., appropriate cable tension and cable displacement) via the handle shuttle during the overall stroke of the handle lever (i.e., input stroke). This optimization may be based on the structure and functionality of the overall jaw closure transmission system including the input sub-system, transmission sub-system, and output sub-system, and in some variations may not be due to just the input sub-system.

The handle mechanism may be designed such that instead of providing a constant mechanical advantage or transmission ratio, it produces a higher transmission ratio (i.e., lower mechanical advantage) in the first portion of the input stroke and a lower transmission ratio (i.e., higher mechanical advantage) in the second portion of the input stroke.

The output sub-system typically includes an end-effector assembly or jaw assembly, and may include the following elements: an end-effector (e.g., jaw) base or end-effector fixed jaw that serves as the local reference or ground; an end-effector movable jaw coupled to the end-effector fixed jaw (e.g., pivotally coupled to the end-effector fixed jaw) such that it can open and close (i.e., displace) with respect to the end-effector fixed jaw.

The full closure displacement of the moving jaw relative to the fixed jaw may be referred to as the output stroke; in the devices described herein, the output stroke is always completed prior to completion of the input stroke, and is generally completed around the transition between the first portion of the input stroke and the second portion of the input stroke (e.g., between about 30% and 70% of the full input stroke, e.g., between about 40% and 60% of the full input stroke, between about 40% and 70% of the full input stroke, between about 45% and 60% of the full input stroke, etc.).

In general, once the jaws have been closed either against themselves or against an object grasped in the jaws, the jaws of the jaw assembly are at a stop position, and will no longer close further (full output stroke), by the action of the handle assembly actuating the transmission cable. However, because the transmission cable has a finite stiffness in a transmission direction (e.g., is somewhat compliant), the handle assembly may continue to be actuated in the second part of the input stroke, and may stretch the transmission cable. This stretch may be felt by the user operating the handle (as resistance in the handle) and the force being applied to stretch the cable may be transmitted to the jaws as a holding force between the jaws.

Thus, a closure displacement of the handle lever relative to the handle body at the input of the closure transmission system may result in a closure displacement of the moving jaw relative to the fixed jaw to hold an object (such as a needle, suture, tissue, staple, clip, etc.) between the jaws.

A pulley coupled to the fixed jaw (e.g., pivotally coupled to the fixed jaw) may be configured to receive the actuation motion from the distal end of the transmission member. The jaw assembly may include a jaw mechanism, which may be a linkage, a cam (e.g., cam surface and pin), etc. The jaw mechanism (e.g., in some variations a drive pin/cam surface) may translate the actuation motion of the jaw pulley relative to the fixed jaw to a corresponding closure motion of the moving jaw relative to the fixed jaw.

In one example of the jaw mechanism, a drive pin is driven by the pulley and interfaces with a camming surface on the moving jaw, providing a camming action. In another example of the jaw mechanism, the distal end of the transmission member (i.e., cable) is wrapped around the pulley. To prevent a potential slippage between the cable and the pulley, there is a positive engagement feature between the cable and the pulley. This is accomplished via a cylindrical member that is crimped onto the cable and sits in a cavity on the pulley. The jaw mechanism is designed to provide a transmission ratio and mechanical advantage between the distal end of the transmission member and the moving jaw, so as to produce the appropriate output displacement and force at the moving jaw relative to the fixed jaw during the overall stroke of the moving jaw (i.e., output stroke). This optimization may be based on the structure and functionality of the overall closure transmission system including the input sub-system, transmission sub-system, and output sub-system, and not just the output sub-system. Specifically, the jaw assembly (end-effector) mechanism may be designed to provide a large mechanical advantage at the end of its stroke, to maximally amplify the force in the transmission member (i.e., tension in the jaw closure transmission cable) to a clamping force at the jaws. This implies that for a certain desired jaw clamping force, the transmission cable tension can be less, which has several advantages.

The transmission sub-system may include a transmission member to transmit the closure action of the input sub-system (i.e., handle assembly) to the output sub-system (i.e., jaw assembly) of the closure transmission system. More specifically, the transmission member may transmit the actuation motion of the handle shuttle to a corresponding actuation motion of the jaw pulley. This transmission member may be a cable, braided rope, etc. that is capable of accommodating very tight bends as might be necessary when the closure transmission system is part of a remote access tool or device.

The transmission member may be highly compliant (i.e., flexible) in bending, twisting, and compression. This member is relatively stiffer in tension because it has to transmit force and displacement along this direction; but at the same time, it is not chosen or designed to be infinitely or effectively infinitely stiff. Rather, it is intentionally designed or chosen to have a finite stiffness (or finite compliance) so that it can also serve as an inline spring. In general, nothing is infinitely stiff or infinitely compliant; infinite stiffness corresponds to zero compliance and zero stiffness corresponds to infinite compliance. Instead, stiffness may be scaled on a relative scale. For example, on some normalized scales a stiffness less than 10 is close to infinitely compliant and a stiffness greater than 1000 is closely to infinitely stiff. In any of the apparatuses described herein, the axial stiffness of the transmission member may have a stiffness in the range of 100.

Any of these apparatuses may include a transmission guide that serves as a conduit or channel (also, a reference) for the transmission member. The proximal portion of this transmission guide is connected to the input sub-system reference (i.e., handle body) and the distal portion of this transmission guide is connected to the output sub-system reference (i.e., end-effector fixed jaw). This guide may be completely rigid in all directions, such as a frame, or a shaft, or tube. Alternatively, this guide may be flexible in bending so that it can take an arbitrary, tortuous shape but still remain very stiff (ideally, close to infinitely stiffness) axially (i.e., along its bent/deformed central axis). This guide may be flexible in bending so that it can take an arbitrary, tortuous shape and have an intermediate stiffness (i.e., have some intentionally finite compliance) in the axial direction (i.e., along its bent/deformed central axis).

The connections between the ends of the guide and respective references of the input and output sub-systems maybe close to infinitely stiff in the transmission direction (i.e., an axial direction of the transmission cable) or may have some intentionally finite compliance (i.e., slightly lower stiffness than infinitely stiff values).

Collectively, the three coupled sub-systems may allow for the use of cables as the primary transmission member. Cables are highly flexible in bending and therefore can be incorporated within minimal access tools/devices that have an input articulation joint between the handle and the tool frame/shaft, and an output articulation joint between the tool frame/shaft and the end-effector. In such devices, the tool frame/shaft may also serve as a portion of the transmission guide, or as the entire transmission guide. In particular, the use of a cable transmission member enables a very tight bend at the output articulation joint, and also helps facilitate the miniaturization of the output articulating joint, and therefore the miniaturization of the end-effector as well at the distal end of the minimal access tool/device.

Furthermore, the choice of a cable as a transmission member and a flexible conduit as a transmission guide member facilitates a minimal access tool/device architecture where the handle assembly is not directly connected to a tool frame/shaft. Instead, in some variations of the devices described herein, the handle assembly "floats" with respect to the tool shaft/frame, and may be connected via a virtual center input articulating joint that is proximal to the handle assembly. The system (apparatus) may include a flexible conduit as the transmission guide member to guide the transmission member (cable) from the handle assembly to the tool shaft/frame.

Furthermore, the choice of a cable as the jaw closure transmission member in an articulating minimal access tool/device may also ensure a relative decoupling between the jaw closure functionality of the device, and articulation functionality of the device. Since the transmission member itself does not have significant bending (i.e., articulation) stiffness, it does not significantly impact the articulation of the end-effector assembly (jaw assembly) about the output articulation joint. Moreover, a large mechanical advantage in the jaw mechanism may result in a lower or limited tension in the transmission cable, which has several advantages listed below. Also, lower tension in the jaw closure transmission cable reduces jumpiness (lateral jerk due to lateral movement of the high tension jaw closure transmission cable) and S-bending (distortion of the joint due to buckling along its center axis) in the output articulating joint.

This overall jaw closure transmission system may enable jaw closure in two steps. During the first portion of the input stroke, as the handle lever moves from its fully open position to an approximately mid-way open position (typically about 30%-70% of the stroke), the moving jaw goes from its fully open position to its fully closed position. In this state, the jaw mechanism has achieved its full output stroke and has reached a hard-stop. This hard-stop may be the result of jaw on jaw contact, or the two jaws holding a needle in between. In either case, the jaw mechanism has reached a static state while there is still input stroke remaining at the handle mechanism. From this point onwards, the remaining stroke of the handle mechanism goes into axially stretching the transmission member (i.e., cable) and/or axially compressing the transmission guide members. The intentional axial compliance selected in the transmission member and transmission guide member (discussed above) enables the user to continue to displace the handle lever through the remaining portion (i.e., the second portion) of the handle mechanism's overall input stroke. During this second portion of the input stroke, the actuation motion of the handle shuttle causes the transmission member (e.g., cable) to stretch and/or the transmission guide member (e.g., flexible conduit) to compress, since the distal end of the transmission member is static due to the static state of the jaw mechanism. Thus, the second portion of the input stroke corresponds to stretching the cable and an associated increase in tension of the cable (based on the compliance of the cable). This gradually increasing cable tension continues to serve as the input force on the jaw mechanism and continues to get amplified by the mechanical advantage of this mechanism (even though the mechanism itself is static due to a hard-stop at the jaws). This means that the clamping force between the jaws (with or without a needle in between) keeps increasing as well. Thus, while the first portion of the input stroke of the handle lever corresponds to an increasing displacement of the moving jaw from a fully-open position to a fully-closed position (i.e., total output stroke), which corresponds to a hard-stop at the jaws (with or without a needle); the second portion of the input stroke at the handle lever corresponds to a gradually increasing clamping force between the jaws (with or without a needle) at the EE assembly. The embodiment may not only be a two-stage stroke, but also may be a three-stage stroke wherein the third stage relates to a region dedicated to facilitating handle lever locking. Within the third stage, the handle lever angular displacement does not produce additional transmission member displacement, and therefore does not introduce any additional energy to the compliant transmission elements. The primary purpose of the third stage is to provide a single region where the handle mechanism locks into place. The presence of this third stage provides an opportunity to optimize handle mechanism design for locking, rather than for facilitating jaw mechanism closure or clamp load generation. Specifically, the input force required throughout the third stage does not depend on the mechanical spring-rate property for the compliant transmission members, but rather merely depends on frictional losses between the members. As a result of isolating transmission sub-system and output sub-system kinematic behavior from the third stage, users of the device will experience a greater consistency of handle mechanism input force. Furthermore, the user input force in the third stage to lock the handle is significantly independent of needle location within the jaws of the output mechanism.

This may result in several benefits for the user in the design, including the substantial reduction in sudden step changes in the force feedback felt by the surgeon at the handle lever as needle contact or jaw contact happens. The presence of transmission member and/or transmission guide member compliance in the axial (i.e., transmission motion) direction makes this transition more gradual and therefore better in feel for the user, compared to a traditional device that has a highly rigid transmission member. This may also result in a reduced number of transmission elements since energy storage functionality is accomplished through the dual-purpose cable and flexible guide members, which play a role in actuation motion transmission as well as serve as energy storing elastic elements. During the second portion of the input stroke of the handle lever, the transmission sub-system efficiently stores energy by means of stretching the transmission cable. This energy storage is not passive, in the sense that the stretching of the cable corresponds to an increase in cable tension, which, when reflected through the mechanical advantage of the EE mechanism, produces an increased jaw clamping force.

In general, the jaw closure transmission systems described herein may be self-limiting and/or self-correcting and/or self-regulating systems for limiting the maximum force that is transmitted via the transmission member in spite of variations in the presence and location of a an object (e.g., needle) in the jaws. This may advantageously lower the loads of all members/components of the jaw closure transmission system. This may also or alternatively lead to less wear, longer life, less chances of failure, more durability etc., and may eliminate the need for complex input, transmission, and output force overload systems that might require additional springs, linkages, and structural members. In addition, these jaw closure transmission systems described herein may regulate needle clamp load, which helps reduce damage to needles, and/or may desensitize the system from a size and location of a needle held between the jaws, and provide an adequate clamping force without damaging the needle. These jaw closure transmission systems may also regulate handle lever force applied by the surgeon which is preferred from an ergonomic standpoint. In the case of a rigid transmission member, it becomes very difficult for the surgeon to regulate the clamping force at the jaws by adjusting his input force/displacement at the handle lever. In such cases, a very small change in the surgeon's input displacement at the handle lever can produce a large, somewhat uncontrolled, change in the clamping force. That is why, in such systems, there are discrete ratchet points between the handle body and handle lever that allows the surgeon to incrementally increase the clamping force at the jaws in controlled amounts. The present jaw closure transmission system, with the intentional use of compliance in the transmission member and transmission guide members, provides the surgeon with a much greater control of the clamping force at the jaws, thus mitigating or eliminating the need for discrete ratchets at the handle lever (with respect to handle body). Rather, this system lets the surgeon rely upon his feel and discretion to regulate input force to achieve a desired needle clamping force. This also eliminates the need for complex multi-lock ratcheting mechanisms in the handle assembly, which otherwise require an additional user actuation component/input to disengage the locking mechanism, without which the tool has to overload the needle or object in the jaws to release it. The handle becomes simpler with a single lock design, as it does not require an additional user input to disengage the lock. Simplifying the handle reduces potential user error and could result in less user training.

Also described herein are jaw closure transmission systems in which an additional intermediate sub-system may be used. FIG. 3 illustrates one example of such a system, showing a handle reference 301, handle mechanism 303, input lever/button 305, first transmission member 307, first transmission guide 309, intermediate transmission mechanism 311, second transmission guide 313, second transmission member 315, and jaw mechanism 317. For example, in addition to an input sub-system and an output sub-system, there may also be an intermediate sub-system with an intermediate mechanism. In that case there may be a first transmission member and transmission guide member between the input and intermediate sub-systems, and a second transmission member and transmission guide member between the intermediate and output sub-systems. The use of an axially compliant transmission and transmission guide member may be preserved to achieve desired jaw closure performance.

In any of the apparatuses described herein the handle input may be a lever, or any other input allowing a variable degree of actuation, and may generally be referred to herein as "levers", including plungers, dials, knobs, etc.

As mentioned, these jaw closure transmission systems may generally provide for connecting an input and an output comprising rigid and compliant transmission elements, as well as rigid and flexible transmission guiding elements, wherein the transmission elements with finite flexibility in the transmission direction also serve to store energy during closure transmission to achieve unique and desirable functionality.

Thus, in a simple form, the system can be thought of as, but not limited to, three sub-systems that are serially connected that take an input, in the form of handle lever displacement by force from the user, and produce an output that presents a moving jaw displacement and clamp load.

The three sub-systems (input sub-system, which is referred to as the handle mechanism; output sub-system, which is referred to as the jaw mechanism; and transmission sub-system, which comprises a transmission member, e.g., cable, and transmission guide, e.g., flexible conduit) may be represented in a system diagram as shown in one example in FIG. 1. The example shown in FIG. 1 includes a handle body or handle shell 101, a handle assembly 103 comprising a handle mechanism having a handle lever 107 (input lever or input link), a transmission guide 109 (rigid pulley) and/or flexible conduit 109', a transmission cable 111, a return spring 113, a fixed jaw 115 (end-effector base/reference) an end-effector assembly 117 comprising a jaw mechanism including a drive pin 121, a pulley pivot pin 123, a pulley 119, and a jaw pivot pin 125.

The input in a handle assembly may comprise a handle body or shell that serves as the local reference or ground. The handle body is generally designed to be ergonomic for the user to hold in various positions since it is generally the articulation of the handle body which controls the location and orientation of the end-effector. Mechanically the handle body can be directly connected to the end-effector via a tool shaft as in straight stick laparoscopic instruments, serially, or connected to the end-effector through an input articulating joint, a tool frame (e.g., a frame, or a frame with a shaft extension, or a shaft), and/or an output articulating joint having a series of joints which provide articulation to the end-effector or even indirectly attached to the end-effector, as described in U.S. Pat. No. 8,668,702. The handle body houses an internal mechanism (or handle mechanism) consisting of a handle lever configured to receive user input in the form of a displacement relative to the handle body. Full handle lever displacement with respect to the handle body is referred to as the input stroke. This input stroke is based on the kinematic design of the handle mechanism and is limited by one or more hard-stops in the handle mechanism. This input stroke is designed to have a specific mechanical advantage curve profile that, when combined with the other sub assembles, is unique to the type of surgical instrument. Generally, for a surgical needle driver, the mechanical advantage curve of the input sub-system initially has a low mechanical advantage and then increases, to have a high mechanical advantage at the end of the input stroke. At full closure, i.e., the end of input stroke, the handle lever reaches a hard-stop relative to the handle body. At this hard stop, there may be a single locking or latching feature that keeps the handle lever latched closed relative to the handle body. As mentioned above, an unlatching/unlocking feature may unlock the handle lever and allow it to open again with respect to the handle body. The output of the handle mechanism is via the handle shuttle 131 (or output member, pull rod, or push rod), which interfaces with the transmission member and provides an actuation motion to the proximal end of the transmission member. The output of the handle mechanism is not limited to a shuttle, the embodiment shown consists of a "shuttle" 131 because the handle mechanism is a 6 bar linkage with a 1 DoF slider joint between the output member (shuttle) and handle body. The handle mechanism is not limited to a 6 bar linkage. The handle mechanism could be a simple lever, 4 bar linkage, cam slot, gear, etc. The handle mechanism may be configured to provide a varying transmission ratio and mechanical advantage between the handle lever and the handle shuttle, so as to produce the appropriate actuation displacement and force at the proximal end of the transmission member (i.e., appropriate cable tension and cable displacement) via the handle shuttle during the overall stroke of the handle lever (i.e., input stroke). The handle mechanism itself may take the form of various configurations. As opposed to a six-bar linkage as cited, in some variations, the linkage system may be a 4-bar linkage, or any alternate system containing a plurality of linkages or motion members that actuates the transmission member either by rotary or linear motion. Conversely, any of the linkages contained within the linkage system could be driven by a cam that is purposefully designed to induce a variable mechanical advantage throughout the handle's jaw closure lever stroke. FIG. 13 shows an input sub-system consisting of a cam (cam surface 1301 and cam transmission member 1305) which achieves the desired variable mechanical advantage. FIG. 13 also shows a shuttle 1307 connected to a shuttle actuation tension member 1309, within the handle body 101. In some variations, the linkage system may be a compliant mechanism that achieves the desired constant or variable transmission ratio. This mechanism may lead to part count reduction by still achieving similar performance. In some variations, the handle mechanism is designed such that instead of providing a constant mechanical advantage or transmission ratio, it produce produces a higher transmission ratio (lower mechanical advantage) in the first portion of the input stroke and a lower transmission ratio (higher mechanical advantage) in the second portion of the input stroke. While the mechanism for input into the input sub-system generally includes an actuating lever body, or ground reference, and a handle input lever, the input sub-system may be embodied alternatively. The input sub-system may be embodied as a motion member capable of translating mechanical energy therein. For example, the input motion member may be a button, dial, tension rod, or binary switch.

The output may generally be a jaw mechanism comprising a jaw base (which may include or be integral) with a fixed jaw that serves as the local reference or ground (alternatively two moving jaws may be used), and the movable jaw may be coupled to the fixed jaw (e.g., pivotally coupled to the fixed jaw) such that it can open and close (i.e., displace) with respect the fixed jaw. The structure of one end-effector (jaw assembly) embodiment is seen in FIGS. 1, 2, 11, 12A, and 12B. As discussed above, the full closure displacement of the end-effector moving jaw relative to the end-effector fixed jaw is referred to as the output stroke. The purpose of this closure displacement of the end-effector moving jaw relative to the end-effector fixed jaw is to hold an object (such as needle, suture, tissue, staple, clip etc.) between the jaws in response to a corresponding closure displacement of the handle lever relative to the handle body at the input of the closure transmission system. The embodiment shown incorporates, but is not limited to, a two-stage mechanical mechanism to produce the desired mechanical advantage curve with the desired mechanical advantage curve having a low mechanical advantage to start with and then having a high mechanical advantage at the end. The design is not limited to the current embodiment as long as the mechanical advantage curve is conserved. In the embodiment shown, an end-effector pulley coupled to the end-effector fixed jaw or the fixed bearing member (e.g., pivotally coupled to the end-effector fixed jaw) is configured to receive the actuation motion from the distal end of the transmission member. A jaw mechanism (e.g., comprising a drive pin/cam surface) may translate the actuation motion of the end-effector pulley relative to the fixed jaw to a corresponding closure motion of the moving jaw relative to the end-effector fixed jaw. In this example of the end-effector mechanism, a drive pin is driven by the end-effector pulley and interfaces with a camming surface 133 on the moving jaw, providing a camming action. Additionally, in this example of the end-effector mechanism, the distal end of the transmission member (i.e., cable) is wrapped around the end-effector pulley. To prevent a potential slippage between the cable and the pulley, there may be a positive engagement feature between the cable and the pulley. This may be accomplished via a cylindrical member that is crimped onto the cable and sits in a cavity on the pulley. Once the cable is wrapped around the pulley, it is connected to a return spring either in the jaw assembly, or on the transmission guide, or in the handle assembly. The purpose of this return spring is to open the jaws after full closure is reached and the handle lever returns to the initial open angle. The end-effector mechanism is designed to provide a varying transmission ratio and mechanical advantage between the distal end of the transmission member and the end-effector moving jaw so as to produce the appropriate output displacement and force at the end-effector moving jaw relative to the end-effector fixed jaw during the overall stroke of the end-effector moving jaw (i.e., output stroke). This optimization is based on the structure and functionality of the overall closure transmission system including the input sub-system, transmission sub-system, and output sub-system, and not just the output sub-system. Specifically, the end-effector mechanism is designed to provide a large mechanical advantage at the end of its stroke, to maximally amplify the force in the transmission member (i.e., tension in the jaw closure transmission cable) to a clamping force at the jaws. This implies that for a certain desired jaw clamping force, if the mechanical advantage of the jaw mechanism is high when the jaws are closed, the transmission cable tension can be lower, which has several advantages. The end-effector may include many different embodiments but is not limited to a pair of jaws, useful for manipulation of needles, suture, tissue, cautery, ligation clip application, etc.

The transmission sub-system may comprise the following elements, a transmission member to transmit the closure action of the input sub-system (i.e., handle assembly) to the output sub-system (i.e., end-effector assembly) of the closure transmission system. More specifically, the transmission member transmits the actuation motion of the handle shuttle to a corresponding actuation motion of the end-effector pulley. This transmission member is a cable, braided rope, etc. that is capable of accommodating very tight bends as might be necessary when the closure transmission system is part of a remote access tool or device as seen in FIGS. 1, 10, 15, and 16. The transmission member is highly compliant (i.e., flexible) in bending, twisting, and compression. This member is relatively stiffer in tension because it has to transmit force and displacement along this direction; but at the same time it is not chosen or designed to be infinitely or effectively infinitely stiff. Rather, it is intentionally designed or chosen to have a finite stiffness (or finite compliance) so that it can also serve as an inline spring. The importance of this finite stiffness for the system level performance is described below. Note that nothing is infinitely stiff or infinitely compliant. Infinite stiffness corresponds to zero compliance and zero stiffness corresponds to infinite compliance. On some normalized scale, a stiffness less than 10 is close to infinitely compliant and a stiffness greater than 1000 is closely to infinitely stiff. On such a scale, a stiffness in the range of 100-200 is where we might place the axial stiffness of the transmission member.

A transmission guide may serve as a conduit or channel (also, a reference) for the transmission member. A proximal portion of this transmission guide is connected to the input sub-system reference (i.e., handle body) and the distal portion of this transmission guide is connected to the output sub-system reference (i.e., end-effector fixed jaw). This guide may be completely rigid in all directions such as a frame, or a shaft, or tube as seen in FIG. 2. This guide may also be flexible in bending so that it can take an arbitrary, tortuous shape but still remain very stiff (ideally, close to infinitely stiffness) axially (i.e., along its bent/deformed central axis). Additionally, this guide may be flexible in bending so that it can take an arbitrary, tortuous shape and have an intermediate stiffness (i.e., have some intentionally finite compliance) in the axial direction (i.e., along its bent/deformed central axis). The connections between the ends of the guide and respective references of the input and output sub-systems may be close to infinitely stiff in the transmission direction (i.e., axial direction of the transmission cable) or may have some intentionally finite compliance (i.e., slightly lower stiffness than infinitely stiff values). FIG. 2 shows a handle assembly 202 comprising a handle mechanism including a handle lever 201 (input link or input lever), a cable 207, a handle body (or handle reference) 203, a return spring 205, a transmission guide member 209, a fixed jaw 211 (end-effector base or reference), an end-effector assembly 213 comprising a jaw mechanism including a pulley 215, a pulley pivot pin 217, a drive pin 219, and a jaw pivot pin 223.

For example, described herein are medical devices having a jaw assembly actuated by a transmission cable having a finite stiffness in a transmission direction. For example the devices may include: an elongate transmission guide, wherein the transmission cable is routed through the transmission guide; a handle assembly at a proximal end of the elongate transmission guide, the handle assembly comprising a handle body, an input lever, a handle output coupled to the transmission cable, and a handle mechanism coupling the input lever to the handle output, wherein the handle mechanism has an input stroke consisting of a full closure displacement of the input lever relative to the handle body, further wherein the input stroke is divided into a first part and a second part, wherein the first part corresponds to a displacement of 30% to 70% of the full closure displacement of the input lever and the second part corresponds to the remaining displacement of the input lever; and wherein the jaw assembly is distal to the elongate transmission guide, the jaw assembly having a first jaw, a second jaw, a jaw input coupled to the transmission cable, and a jaw mechanism coupling the jaw input to the second jaw, wherein the jaw mechanism has an open configuration when the first and second jaws are fully open relative to each other and a closed configuration when the first and second jaws are fully closed; further wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the handle lever relative to the handle body corresponding to the second part of the input stroke stretches the transmission cable, wherein the resulting tension in the transmission cable is converted by the jaw mechanism to a holding force between the first and second jaws.

A medical device having a jaw assembly actuated by a transmission cable having a finite stiffness in a transmission direction may include: an elongate transmission guide comprising a flexible conduit, wherein the transmission cable is routed through the transmission guide; a handle assembly at a proximal end of the elongate transmission guide, the handle assembly comprising a handle body, an input lever, a handle output comprising a shuttle coupled to the transmission cable, and a handle mechanism comprising a six bar linkage coupling the input lever to the handle output, wherein the handle mechanism has an input stroke consisting of a full closure displacement of the input lever relative to the handle body, further wherein the input stroke is divided into a first part and a second part, wherein the first part corresponds to a displacement of 30% to 70% of the full closure displacement of the input lever and the second part corresponds to the remaining displacement of the input lever; and wherein the jaw assembly is distal to the elongate transmission guide, the jaw assembly having a first jaw, a second jaw, a jaw input comprising a pulley coupled to the transmission cable, and a jaw mechanism comprising a cam surface between the jaw input and the second jaw, wherein the jaw mechanism has an open configuration when the first and second jaws are fully open relative to each other and a closed configuration when the first and second jaws are fully closed; further wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the handle lever relative to the handle body corresponding to the second part of the input stroke stretches the transmission cable, wherein the resulting tension in the transmission cable is converted by the jaw mechanism to a holding force between the first and second jaws.

The handle mechanism may be a linkage (e.g., six-bar linkage, four-bar linkage, etc.) or a cam (cam surface and pin, etc.). In general, the elongate transmission guide may comprise a flexible conduit or elongate shaft or both.

The transmission cable may generally have a finite stiffness in the direction of transmission (e.g., along the length of the extended cable). For example the transmission cable may have a stiffness in a transmission direction of less than 800 pounds per inch, less than 700 pounds per inch, less than 650 pounds per inch, less than 600 pounds per inch, less than 500 pounds per inch, less than 400 pounds per inch, etc. (and in some variations be greater than 100 pounds per inch, greater than 150 pounds per inch, greater than 200 pounds per inch, greater than 250 pounds per inch, greater than 300 pounds per inch, etc., e.g., between 100 and 650 pounds per inch, etc.).

In any of these apparatuses (devices, systems, mechanism, tools, etc.) the handle mechanism may be configured to provide a first mechanical advantage during the first part of the input stroke and a second mechanical advantage that is greater than the first mechanical advantage during the second part of the input stroke. The handle output may comprise one or more of: a shuttle, a push rod, or a pull rod. The device may include a jaw base to which either or both the first and second jaws are pivotally coupled.

The jaw input may comprise a jaw pulley, and the jaw mechanism may comprise a cam surface between the jaw pulley and the second jaw.

As mentioned above, any of these devices may include a releasable latching mechanism configured to hold the handle lever locked in a closed position at the end of the input stroke.

Also described herein are methods of using any of the apparatuses including these jaw closure transmission systems. For example, described herein are methods of operating a medical device to close a jaw assembly of the medical device, wherein the medical device comprises an elongate transmission guide, a finite stiffness transmission cable within the transmission guide, and a handle assembly at the proximal end of the elongate transmission guide having an input lever and a handle mechanism coupling the input lever to the transmission cable, wherein the transmission cable is coupled to a jaw input of the jaw assembly, wherein the jaw assembly is distal to the elongate transmission guide. The method may include: actuating the input lever to apply tension to the transmission cable during a first part of an input stroke of the handle assembly to close a first and second jaw of the jaw assembly from an open configuration until the first and second jaws reach a hard stop; and continuing to actuate the input lever during a second part of the input stroke after the first and second jaws have reached the hard stop, and stretching the transmission cable; wherein the input stroke consists of a full displacement of the handle lever of the handle assembly, and further wherein the handle assembly transitions from the first part of the input stroke to the second part of the input stroke when the handle is between 30% and 70% displaced.

A method of operating a medical device to close a jaw assembly of the medical device (wherein the medical device comprises an elongate transmission guide, a finite stiffness transmission cable within the transmission guide, and a handle assembly at the proximal end of the elongate transmission guide having an input lever and a handle mechanism coupling the input lever to the transmission cable, wherein the transmission cable is coupled to a jaw input of the jaw assembly, and wherein the jaw assembly is distal to the elongate transmission guide) may include: actuating the input lever to actuate the transmission cable during a first part of an input stroke of the handle assembly and translate the transmission cable relative to the elongate shaft to close a first and second jaw of the jaw assembly from an open configuration until the first and second jaws reach a hard stop; and continuing to actuate the input lever and stretching the transmission cable without translating the first or second jaws during a second part of the input stroke after the first and second jaws have reached the hard stop; wherein the input stroke consists of a full displacement of the handle lever of the handle assembly, and further wherein the handle assembly transitions from the first part of the input stroke to the second part of the input stroke when the handle is between 30% and 70% displaced.

Any of these methods may include applying a first mechanical advantage during the first part of the input stroke and applying a second mechanical advantage that is greater than the first mechanical advantage during the second part of the input stroke. These methods may also include grasping an object between the first and second jaws, wherein the first and second jaws reach the hard stop when the object is secured between the first and second jaws.

Any of these methods may also include locking the input lever in a fully closed position relative to a handle shell in the handle assembly.

Any of these methods may also include releasing the input lever to transition the handle lever from the second part of the input stroke to the first part of the input stroke, reducing the tension on the transmission cable and reducing the stretch of the transmission cable before translating the transmission cable so that the first and second jaws open. Actuating the input lever may comprise squeezing the input lever.

As mentioned, these jaw closure transmission systems may be integrated into any appropriate apparatus. For example, any of these apparatus may be configured as a medical device, see for example FIGS. 15 and 16, including a jaw closure transmission system. For example, a medical device having a distal jaw assembly actuated by a transmission cable having a finite stiffness in the transmission direction and that is compliant in bending may include: a tool frame comprising an elongate shaft and a forearm attachment region at a proximal end of the tool frame configured to couple with an arm attachment cuff; a handle assembly, the handle assembly comprising a handle shell configured to be gripped in a user's palm and an input lever on the handle shell, wherein the handle shell encloses a handle linkage coupling the input lever to the transmission cable through a handle output, further wherein the handle assembly has an input stroke consisting of a full closure displacement of the input lever from an undisplaced configuration to a fully displaced configuration, further wherein the input lever transitions from a first part of the input stroke to a second part of the input stroke when the input lever is displaced from an undisplaced configuration to between 30% and 70% of its full closure displacement configuration; an input joint between the handle and the tool frame configured to encode motion of the handle about a pitch axis of rotation relative to the tool frame for transmission to an articulating output joint, and further configured to encode motion of the handle about a yaw axis of rotation relative to the tool frame for transmission to the articulating output joint, wherein the pitch axis of rotation and the yaw axis of rotation intersect in a center of rotation; wherein the jaw assembly is coupled to the distal end of the elongate tool shaft by the articulating output joint, the jaw assembly having a first jaw, a jaw pulley pivotally coupled to the first jaw and further coupled to the transmission cable, a second jaw pivotally coupled to the first jaw, and a cam surface that translates motion of the jaw pulley to a motion of the second jaw relative to the first jaw, wherein the jaw assembly has an output stroke that extends from an open configuration when the first and second jaws are fully open to a closed configuration when the first and second jaws are fully closed; wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the handle lever relative to the handle body corresponding to the second part of the input stroke stretches the transmission cable, wherein the resulting tension in the transmission cable is converted by the jaw mechanism to a holding force between the first and second jaws; and a transmission guide extending between the handle assembly and the elongate shaft, wherein the transmission cable extends from the handle assembly, through the transmission guide to the jaw assembly. FIGS. 10, 14, 15 and 16 illustrate one example of such an apparatus.

In FIG. 10, a medical device apparatus includes a jaw closure transmission as described above. The exemplary apparatus includes a tool frame 525, which includes a tool shaft 526 and a forearm attachment portion at the proximal end 527. A cuff (not shown) having a passage therethrough that is configured to hold a wrist or forearm of a user may be coupled to the forearm attachment portion, in some variations via a bearing between the forearm attachment portion of the frame and the cuff that is configured to slide or roll so that there is a roll rotational degree of freedom between the frame and the cuff about the tool axis. A proximal handle assembly may be connected to the tool frame by an input joint. The input joint may be configured to encode motion between the tool frame and the handle assembly, as shown in FIG. 10. In this example, the input joint includes a pair of transmission strips 533, 534 that connect to respective pivoting joints (not shown) in parallel to separately encode pitch and yaw rotations of the handle assembly. The output joint 583 (an end-effector articulation joint configured as a jaw assembly), as shown in FIG. 14, may be any of the multi-cluster joints described herein and is between the jaw assembly and the tool frame (e.g., tool shaft) and receives transmission input (e.g., cables, not shown) from the output joint (including transmission strips 533, 534 of the output joint) to articulate the jaw assembly.

In this example, the handle assembly includes an ergonomic palm grip portion 501 (handle shell) that connects to the rotation dial 502. The handle assembly also includes a control (lever) 549 input (in this example, defining the end-effector jaw closure input 549') that is configured as a handle lever and acts as a rigid extension of the internal push rod. A transmission cable 566 connects to the shuttle and acts as a jaw closure actuation transmission member extending from the shuttle and through the tool shaft 526 to the jaw assembly. This transmission cable may be enclosed by a protective and/or supporting sheath or cover or conduit, for some or the entire portion of its length. The end-effector is a jaw assembly including a first (ground) end-effector portion, in this example, including a fixed jaw 569 to which a pivoting second end-effector portion (moving jaw 568) is attached. The transmission cable 566 may couple to the moving jaw 568 at the end-effector closure output 577.

In FIG. 10, rotation of the dial portion 502 of the handle assembly when the user's forearm is mounted to the proximal end and the palm grip region 501 is held in the user's hand so that the user can rotate the dial between the thumb and fingers, rotates the entire tool frame, and therefore the end-effector that is attached to the distal end of the tool shaft 526 via an end-effector output articulating joint 583. Thus, the handle may rotate about first axis 511, referred to as the handle articulated roll axis (axis 1), to cause the tool shaft to rotate in a third axis 515, referred to as the tool shaft roll axis (axis 3), in turn causing the end-effector to roll about a second axis 513, referred to as an end-effector articulated roll axis (axis 2).

The rotation dial 502 as shown in FIG. 10 is rotated about the first axis 511. The rotation leads to rotation of tool frame 525 via transmission strips 533, 534 (as they constrain rotation DoF), rotation of the tool shaft 526 (about the third axis 515), and therefore, the rotation of the end-effector (about the second axis 513). When the handle is articulated using the input articulating joint, the output joint (multi-cluster joint 583) and the end-effector articulate via the output articulating joint 583. The center axis (axis 2) 513 for the end-effector is different from the axis 3, the shaft axis 515. The intermediate transmission mechanism consists of but is not limited to a cam mechanism as seen in FIG. 3B. The intermediate transmission mechanism could be a linkage, gear, cog etc. During stroke A, the force is not being amplified through the intermediate transmission mechanism, however at the transition from stroke A to stroke B the first transmission member lifts off the hub 353 and rides a surface farther away from the cam's center of rotation, creating a force amplification from the first transmission member to the second transmission member. This force amplification increases the mechanical advantage of the system. This mechanism is shown in the structure of the device in FIG. 3C (e.g., including transmission cam 361, transmission members 362, return pulley 363 and return spring 364). While this transmission system invention is specifically embodied as a laparoscopic, endoscopic, or other minimally invasive surgical jaw closure device, it is understood that those skilled in the art can alternately translate the invention, without departing from the scope, to alternate embodiments for transmission systems such as those that require end-effector clamping action like grasping, holding, or clamping instruments.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 11, the end-effector assembly may include a movable jaw 1101 (having an engagement surface 1102, jaw pivot 1103, clearance slot 1104, and drive slot 1105), a pulley 1107 (having a drive pin 1108) that connects to a cable 1109, and a fixed jaw 1111 (having an engagement surface 1112, pulley pivot pin 1114, and movable jaw pivot pin 1113).

DETAILED DESCRIPTION

Figure 1:
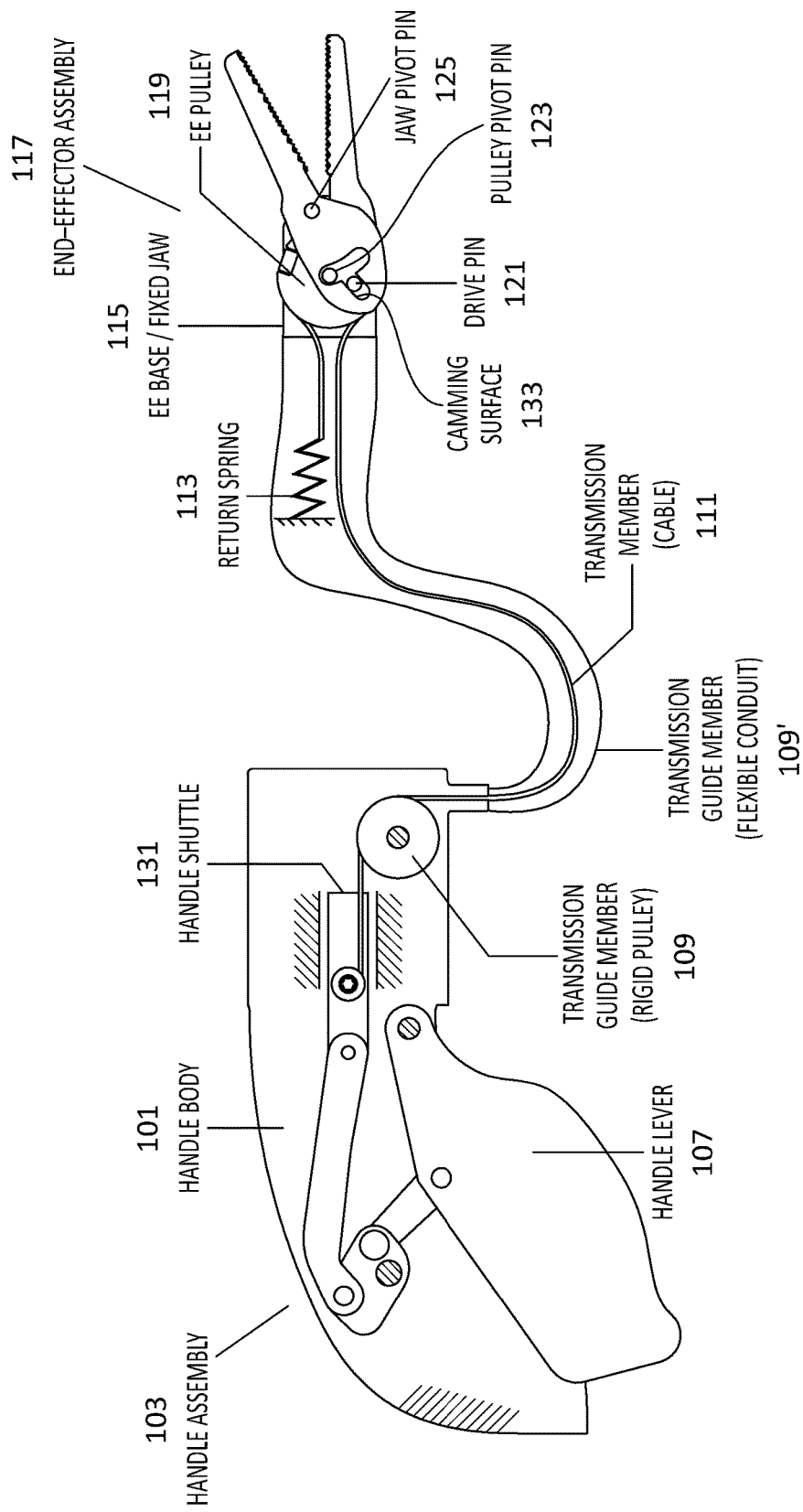
FIG. 1 shows an example of a system diagram of a jaw closure transmission system consisting of an input sub-system, a flexible transmission sub-system and an output sub-system.
Figure 2:
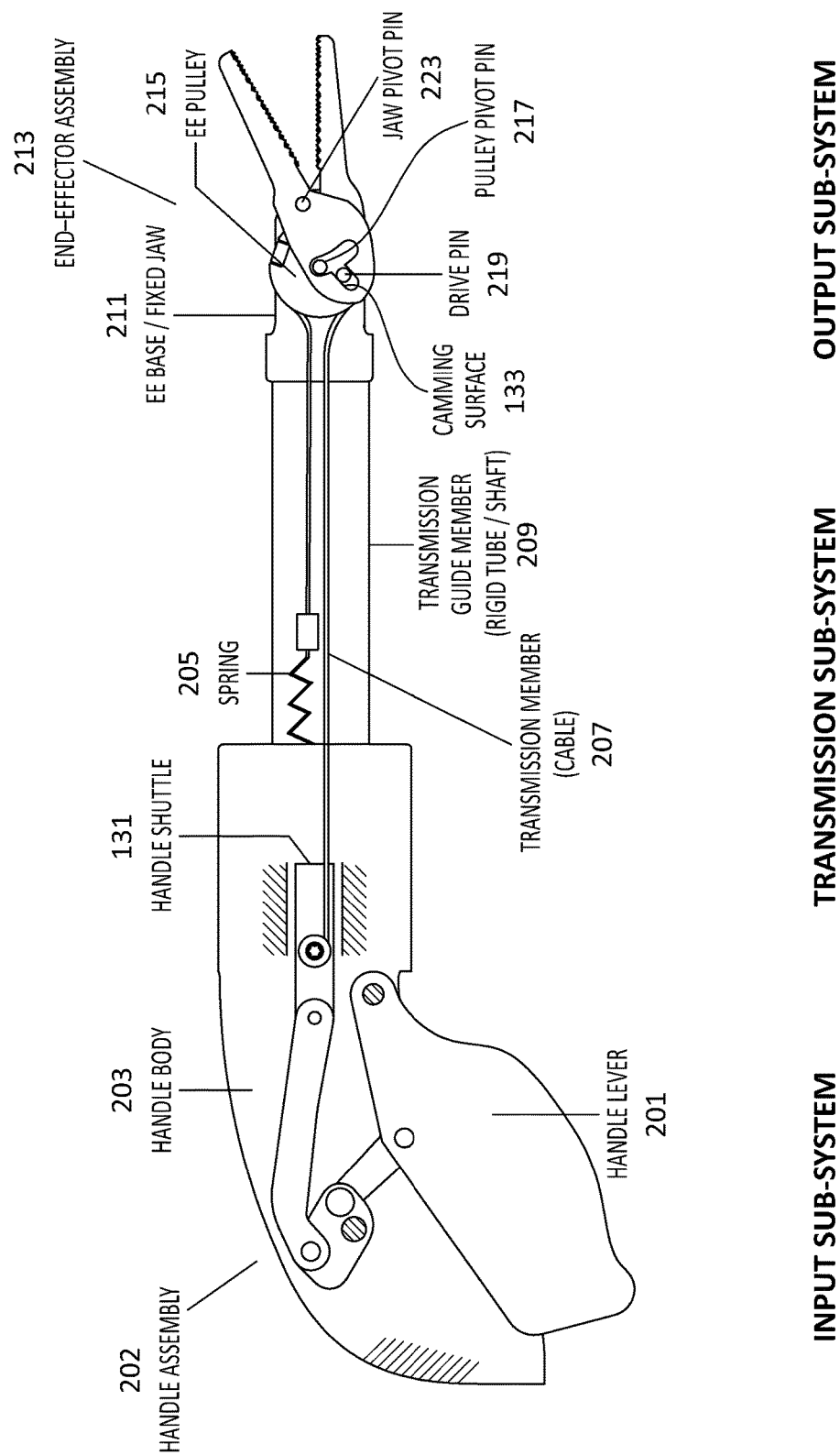
FIG. 2 is another diagram showing an example of a jaw closure transmission system consisting of an input sub-system, a rigid transmission sub-system and an output sub-system.
Figure 3:
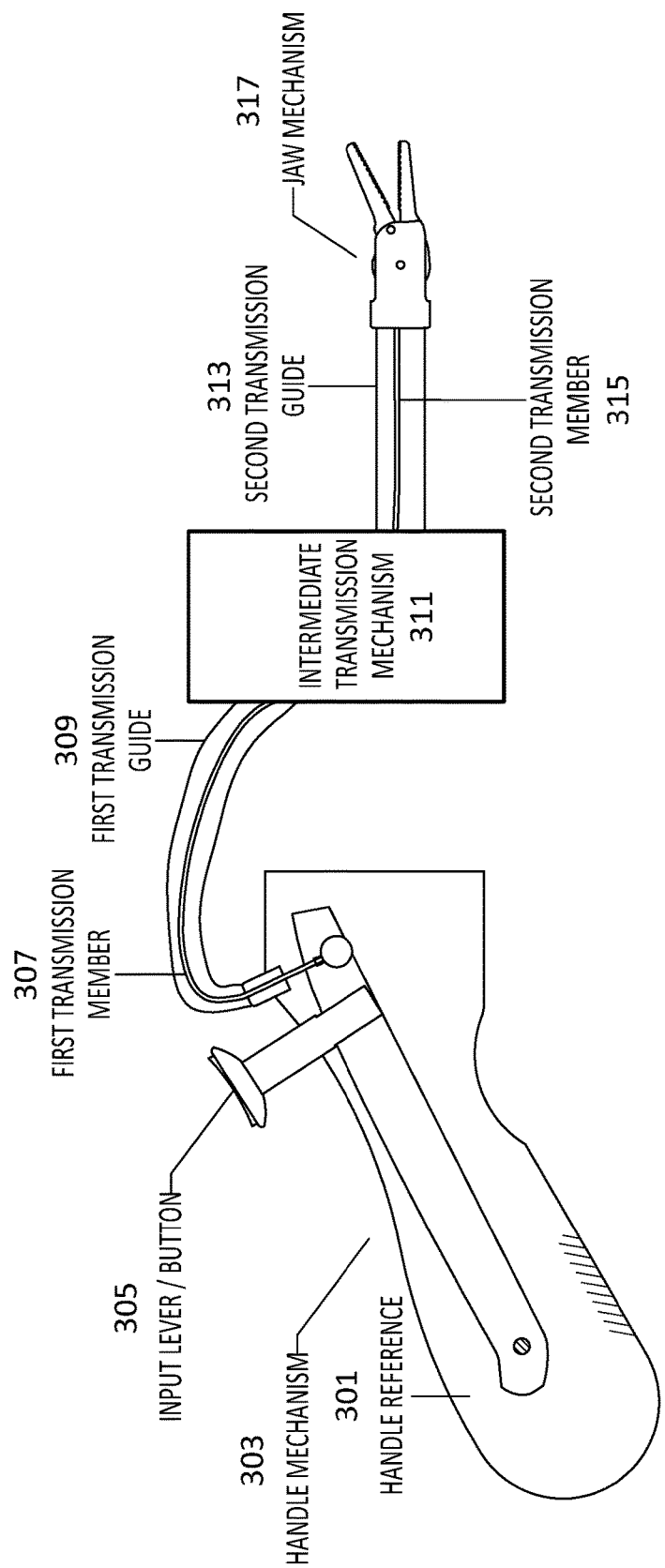
FIG. 3 is another diagram showing an example of a jaw closure transmission system with an intermediate transmission mechanism incorporated into the jaw closure transmission system.
Figure 3B:
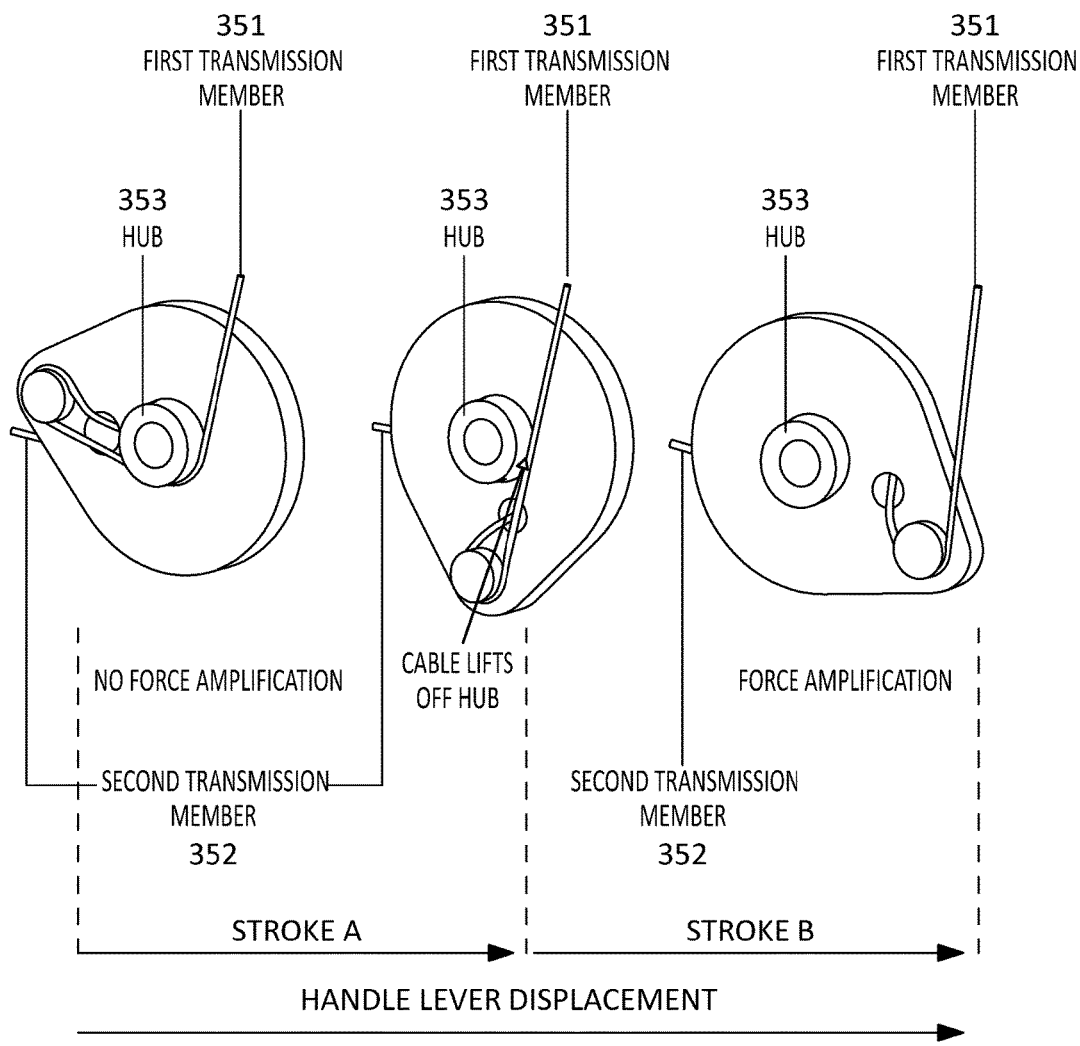
FIG. 3B shows an embodiment of an intermediate transmission cam used to create a force amplification from the first transmission member 351 to the second transmission member 352.
Figure 3C:
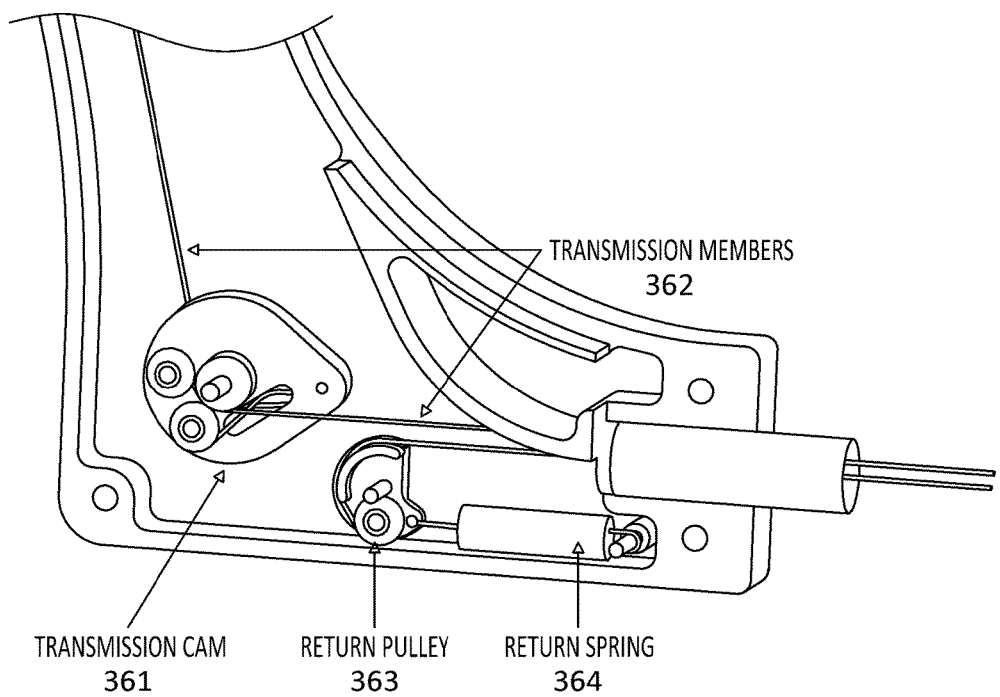
FIG. 3C shows an embodiment of an intermediate transmission mechanism located inside a device/tool.
Figure 4:
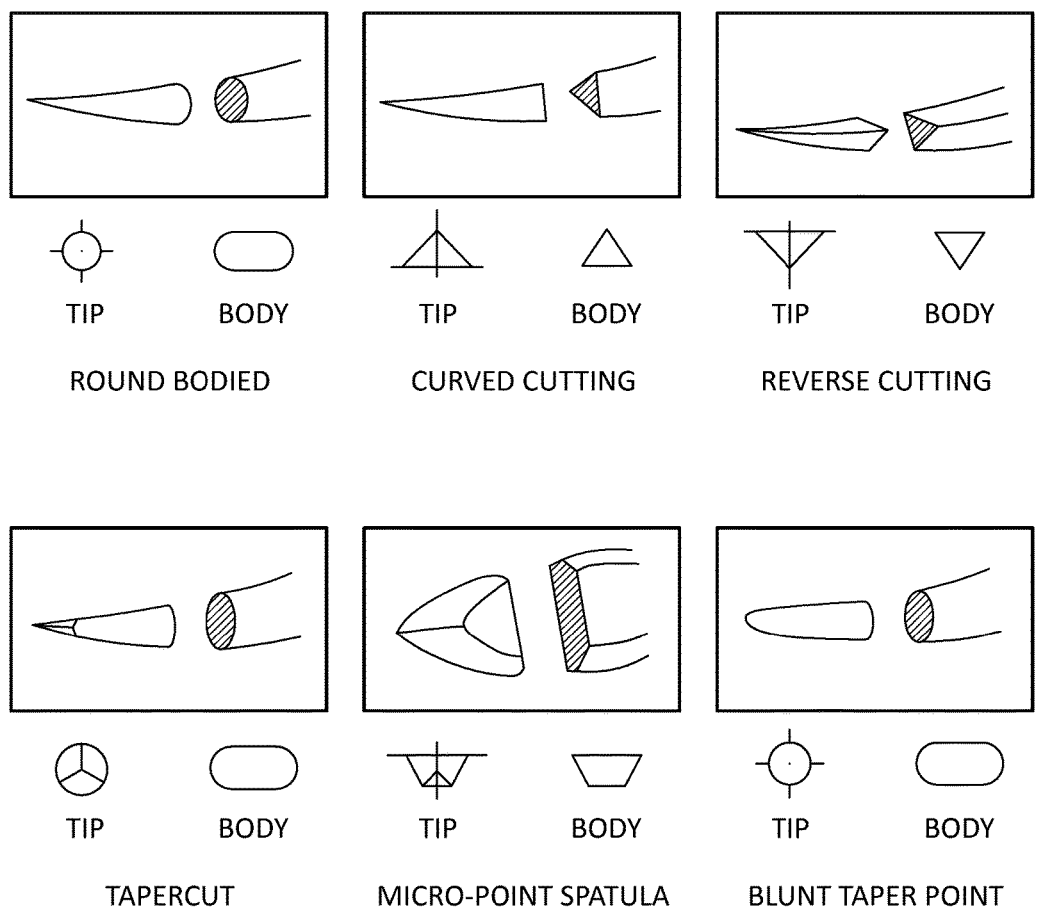
FIG. 4 shows various cross-sections for needles that are commonly used in minimally invasive surgery and that may be grasped by an apparatus including any of the jaw closure transmission systems described herein.

Described herein are jaw closure transmission systems and apparatuses including them. For example, described herein are transmission systems (jaw closure transmission systems) for a remote access tool which incorporates a transmission member with finite transmission direction stiffness (or equivalently, a compliant transmission member) that interfaces with the input and output mechanisms of the remote access tool. A relatively stiff transmission member of known use in medical devices can't be replaced with a compliant transmission member to achieve the performance described herein. The transmission system in its entirety must be designed in unison to achieve the performance that will be described. The performance of the transmission system in its current configuration is specific for a needle driver. Surgical needle drivers are typically one handed operation devices which require high clamping loads at jaw clamping surfaces in order to drive various needles through tissues. It is important to understand the various types of needles because the design of a compliant transmission member can protect the needle from damage when over-driving the jaws. FIG. 4 shows various needle types that are selected based on the medium that they are driven through. The body of the needle is just as important as the tip, in that, as the needle is driven through the tissue, there is an interaction between the needle in its entirety and the tissue. The jaws of a needle driver are designed with a pattern intended to increase the needle retention without requiring high jaw clamping loads. However, if a large enough clamping load is applied to the needle, the clamping surfaces will damage the needle body, leaving permanent impressions on the needle surface. When the surface of the needle is damaged, it will no longer slide smoothly through the tissues, which will result in resistance felt by the surgeon and unnecessary damage to the patient.

Figure 5:
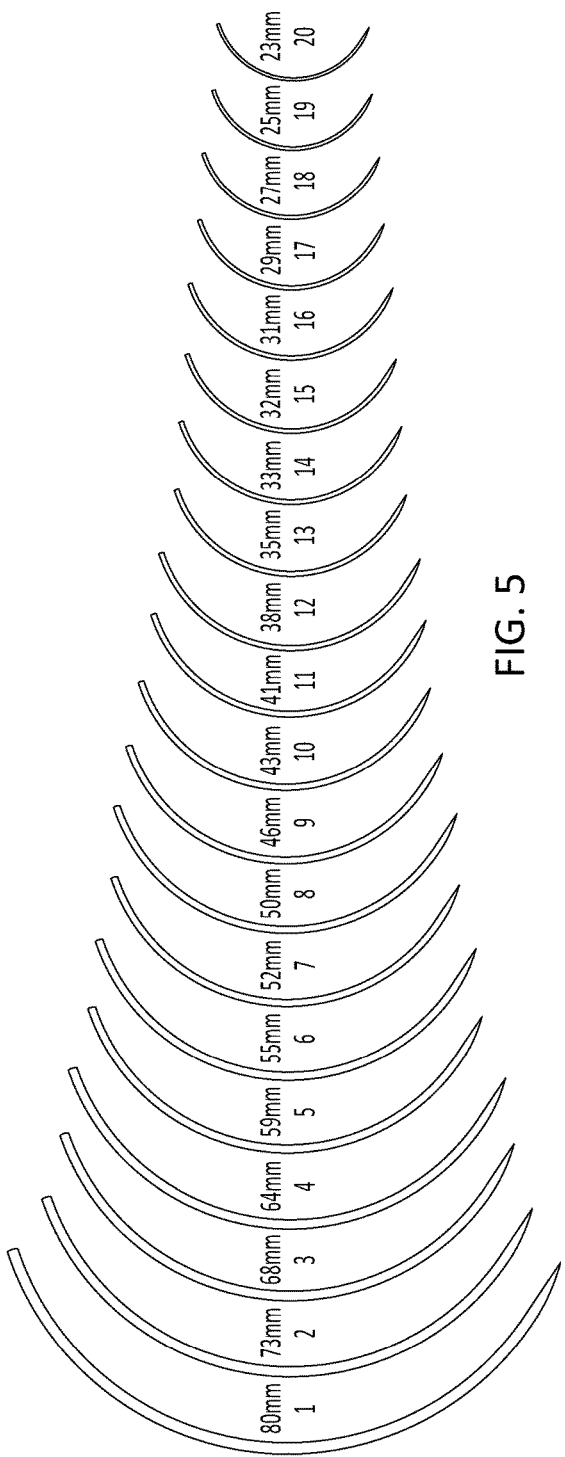
FIG. 5 illustrates various needle sizes that are commonly used in minimally invasive surgery.
Figure 7:
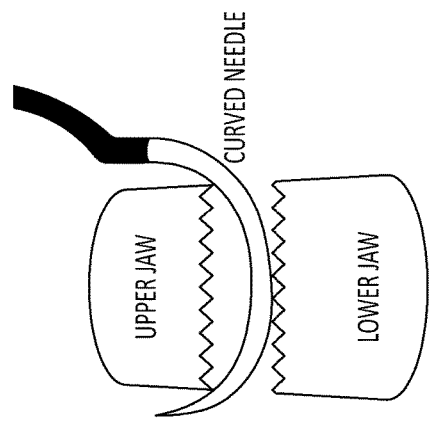
FIG. 7 is a front view of needle driver jaws clamping down on a curved needle.
Figure 6:
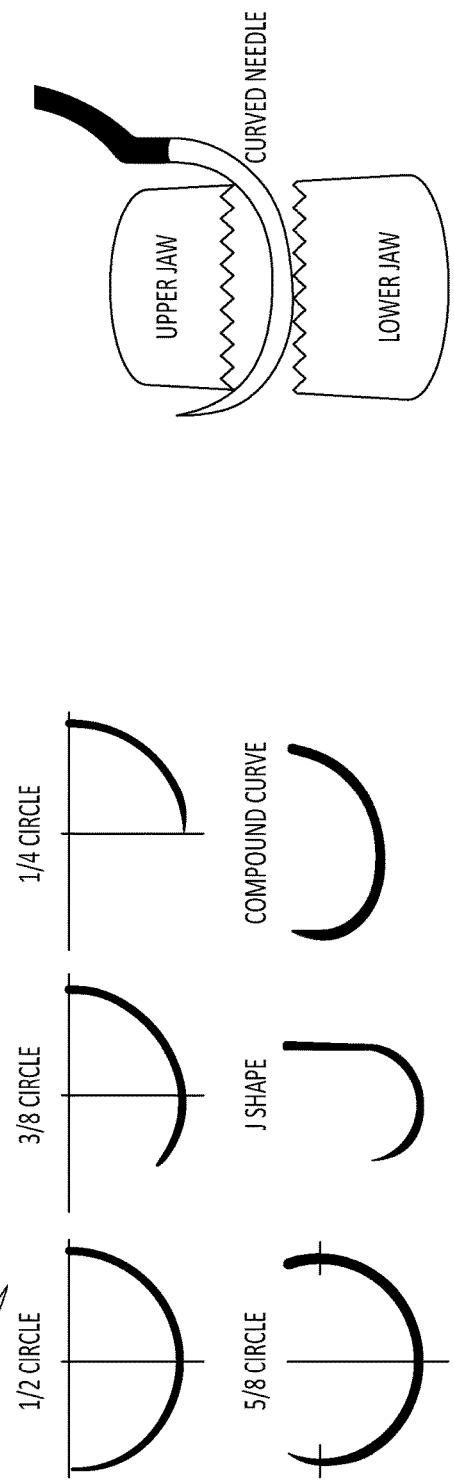
FIG. 6 shows various needle geometries that are commonly used in minimally invasive surgery.

In addition to surface damage on the needle, an overload in clamping force could cause the shape of the needle to permanently deform. Needles used for minimally invasive surgery also come in various shapes and sizes, as seen in FIG. 5 and FIG. 6 respectively. The jaws of the needle driver are designed to be wide enough to not allow the needle to rotate; as a result, needles with a larger curve and smaller diameter can be easily deformed and straighten out by large clamping loads. FIG. 7 showed a curved needle being held by the upper and lower jaws of a needle driver; as a larger clamping load is applied, the needle would straighten in that region due to three-point bending, causing the needle to not drive through the tissue in a true arc.

The needle location in the jaws also influences the corresponding jaw clamping force and impacts its ability to adequately secure a needle. The needle can be placed anywhere along the jaw length which could mean at the very tip of the jaws or at the mouth of the jaws; this significantly changes the effort required by the user to actuate the input mechanism completely to full stroke. In some configurations full stroke should not be achieved due to potential damage to the needle, therefore typical needle drivers incorporate an input ratcheting system, where the stroke of the handle can be broken up into finite segments in between ratchets to allow the user to hold the needle at various input lever locations.

Figure 8:
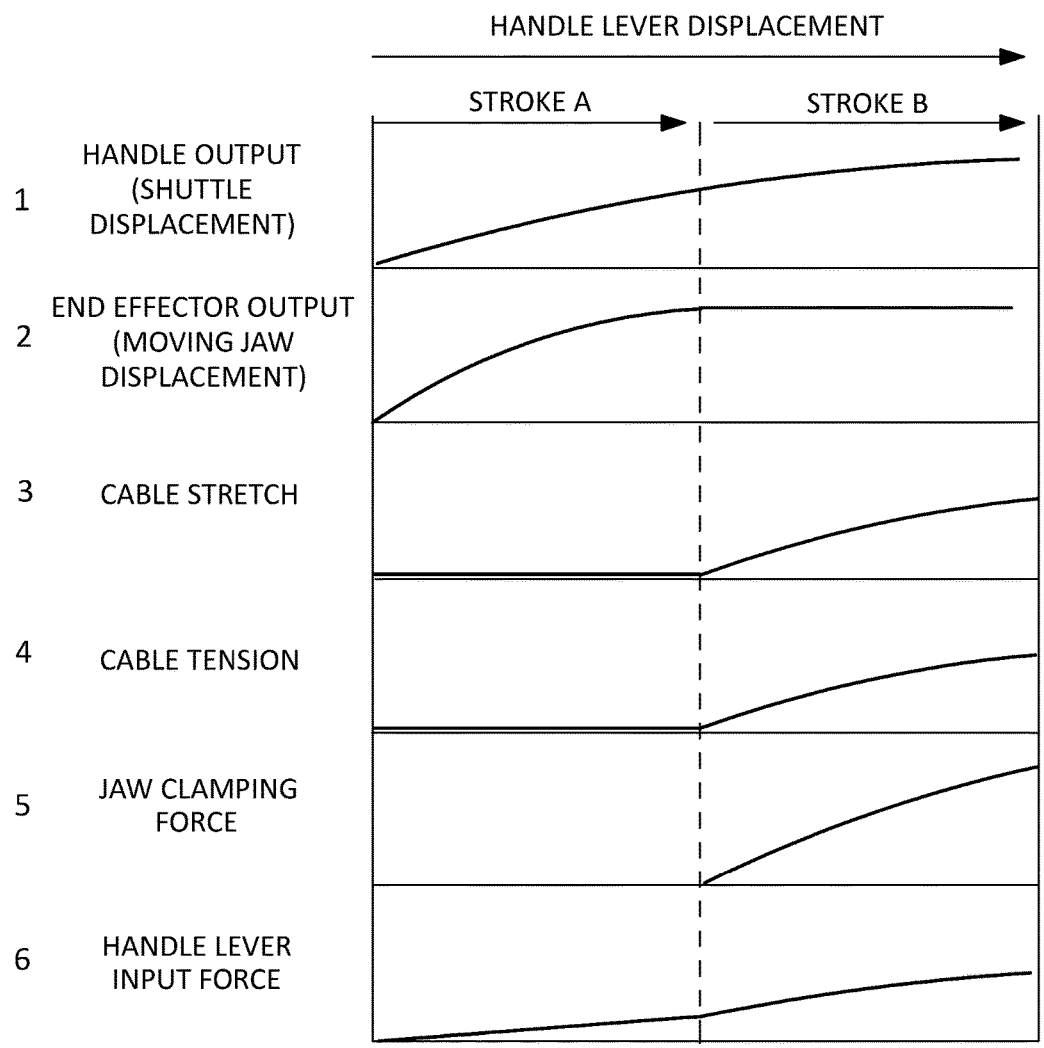
FIG. 8 shows graphs illustrating the transmission system of a needle driver's input stroke.

The use of a compliant transmission member solves these problems and eliminates the discrepancy among uses users in the amount of input used to adequately hold the needle. A compliant transmission member acts as an energy storage member so that the user can actuate the input handle lever completely without having to worry about over-driving the jaws and damaging the needle. If a large needle is placed within the mouth of the jaws, a full stroke can still be achieved at the handle input lever while in a needle driver with a stiff transmission member, full stroke would not be achievable without causing damage to the instrument or the needle. This reduces the need for a multiple ratchet system which can provide discrepancies to users on whether adequate jaw clamping force is achieved. The handle lever displacement (input stroke) can be broken up into two different phases, stroke A and stroke B. Whereas the transition from stroke A to stroke B occurs when the jaws reach a hard stop, such that stroke A is before jaw hard stop and stroke B is after the jaw hard stop. Jaw hard stop could occur at various handle lever displacements depending on the needle type, needle location or even needle presence. FIG. 8 shows various graphs that help explain what happens in the system as a fully input stroke is achieved.

Figure 9:
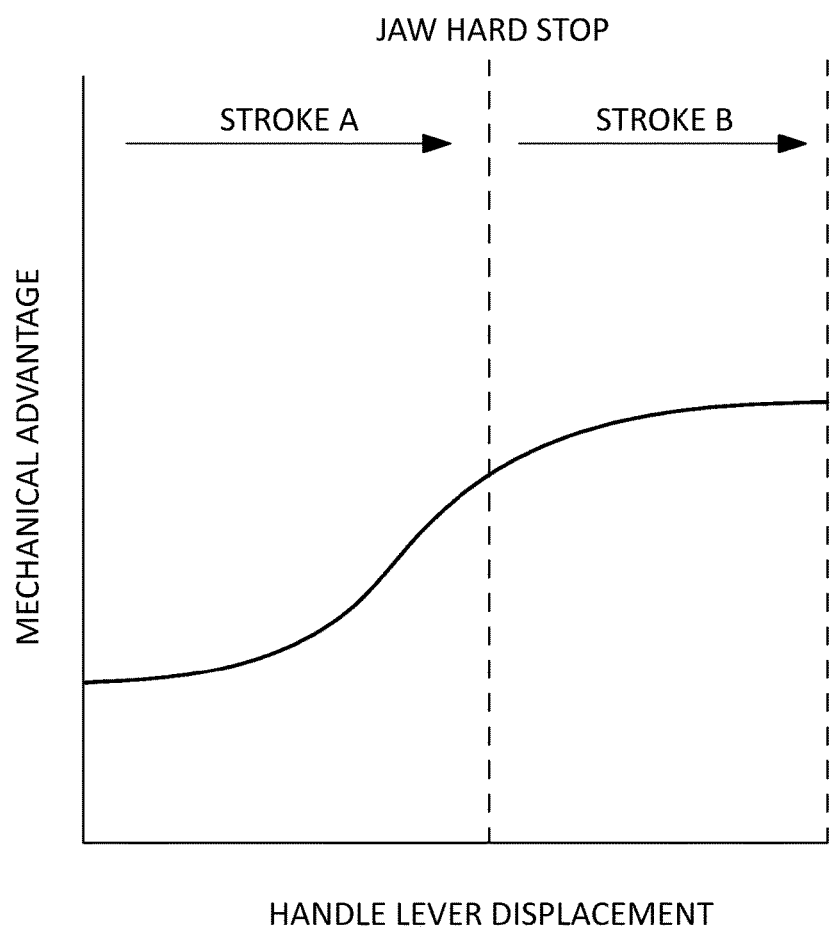
FIG. 9 shows a mechanical advantage profile for the entire system as a function of the input handle lever displacement.
Figure 10:
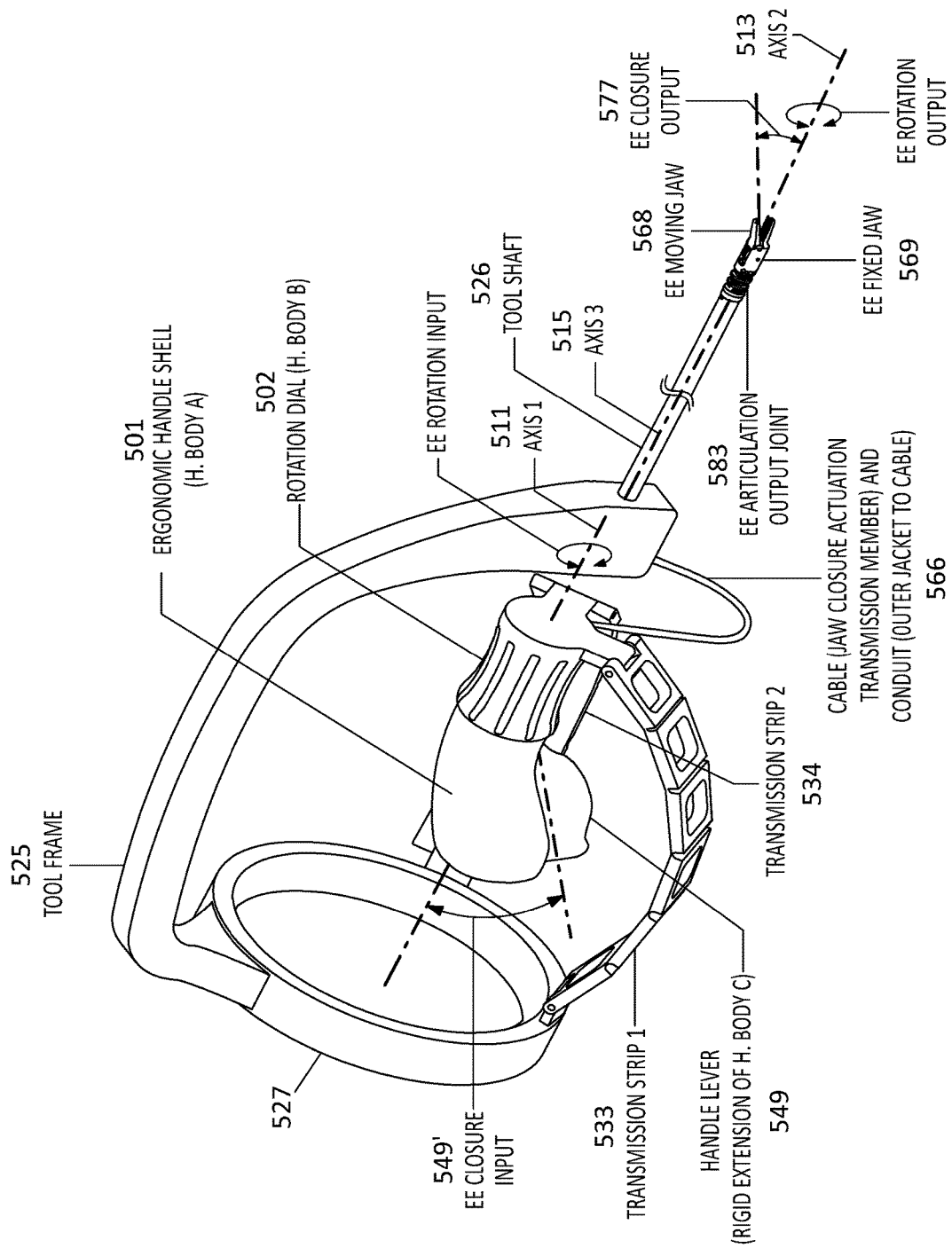
FIG. 10 illustrates one example of a medical device incorporating a jaw closure transmission system as described herein.
Figure 11:
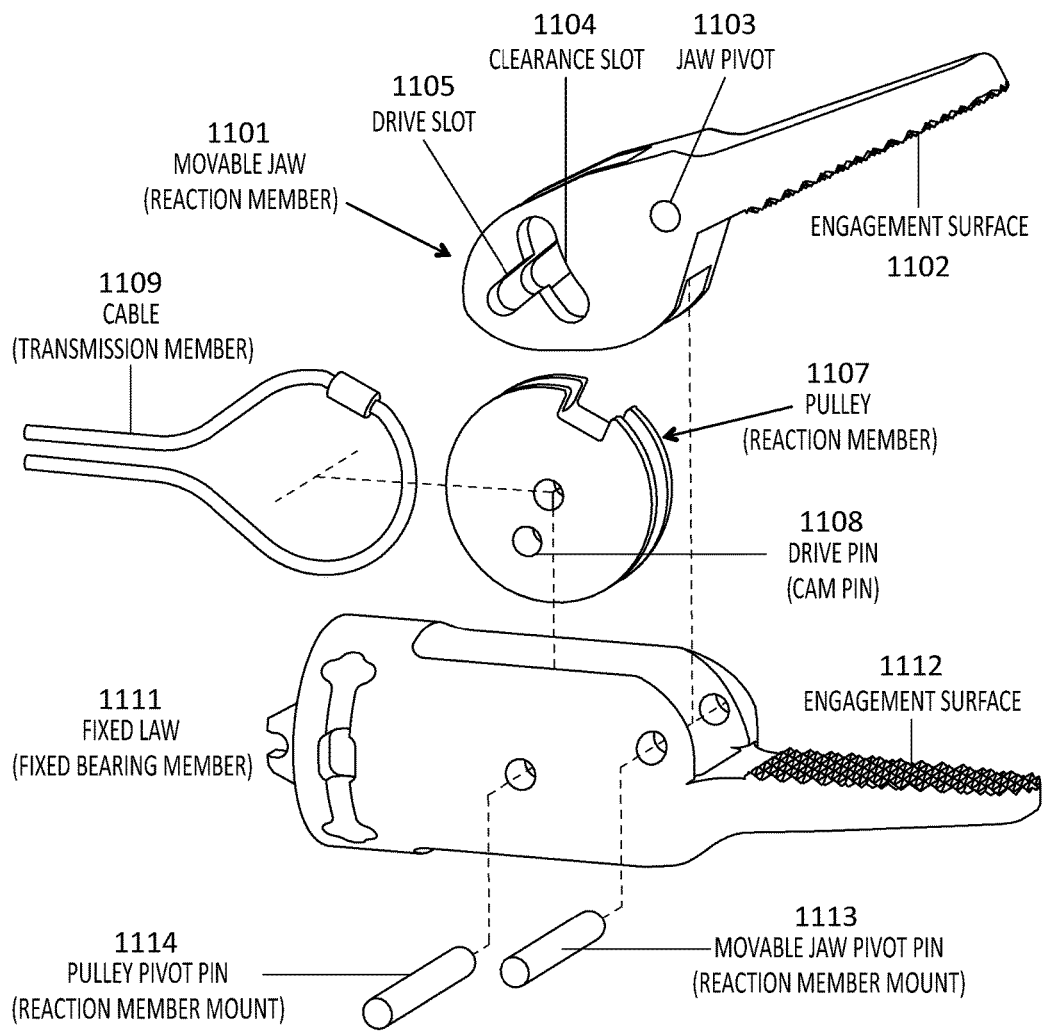
FIG. 11 shows an exploded view of an end-effector assembly.
Figure 12A:
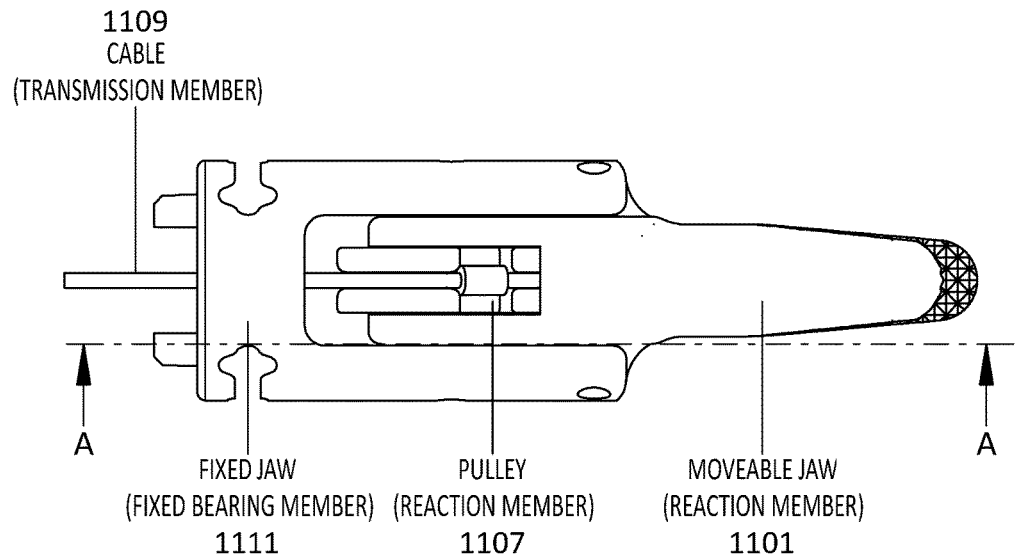
FIG. 12A shows a detailed view of an end-effector assembly where the moveable jaw is in open condition.
Figure 12A:
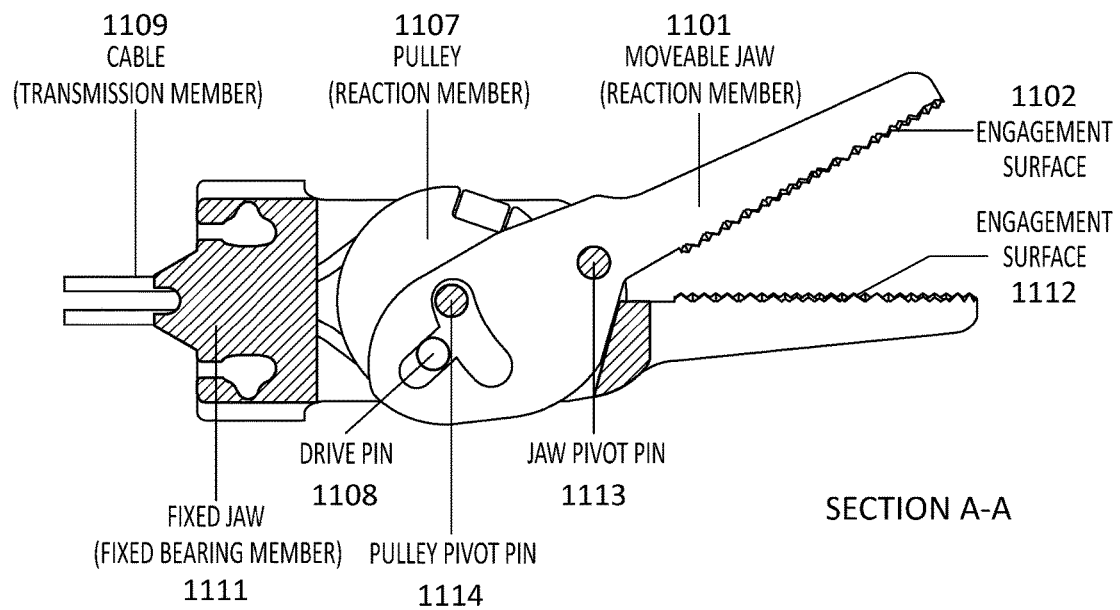
Figure 12B:
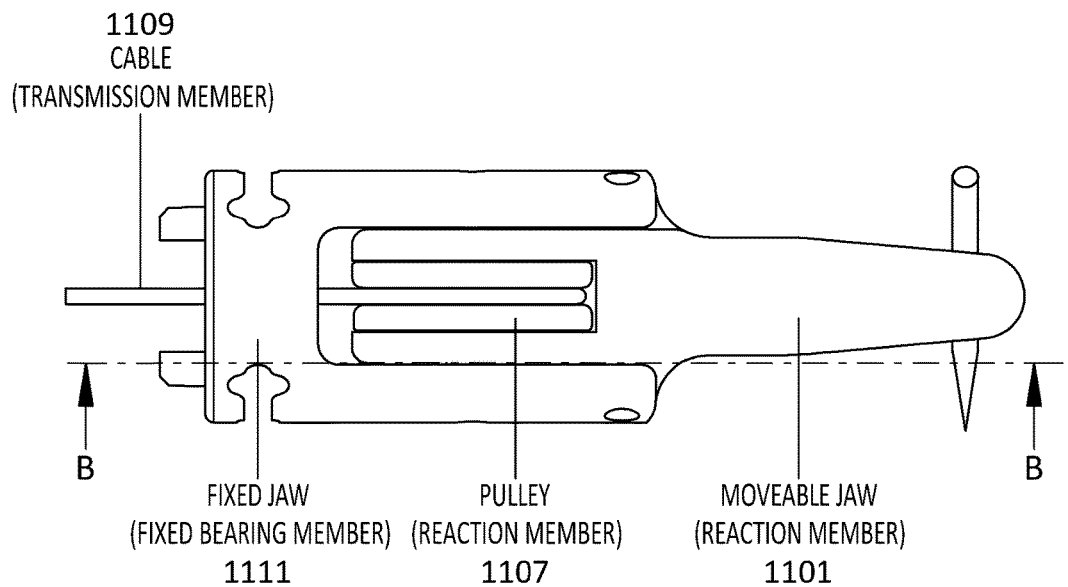
FIG. 12B shows a detailed view of an end-effector assembly where the moveable jaw is grasping a needle.
Figure 12B:
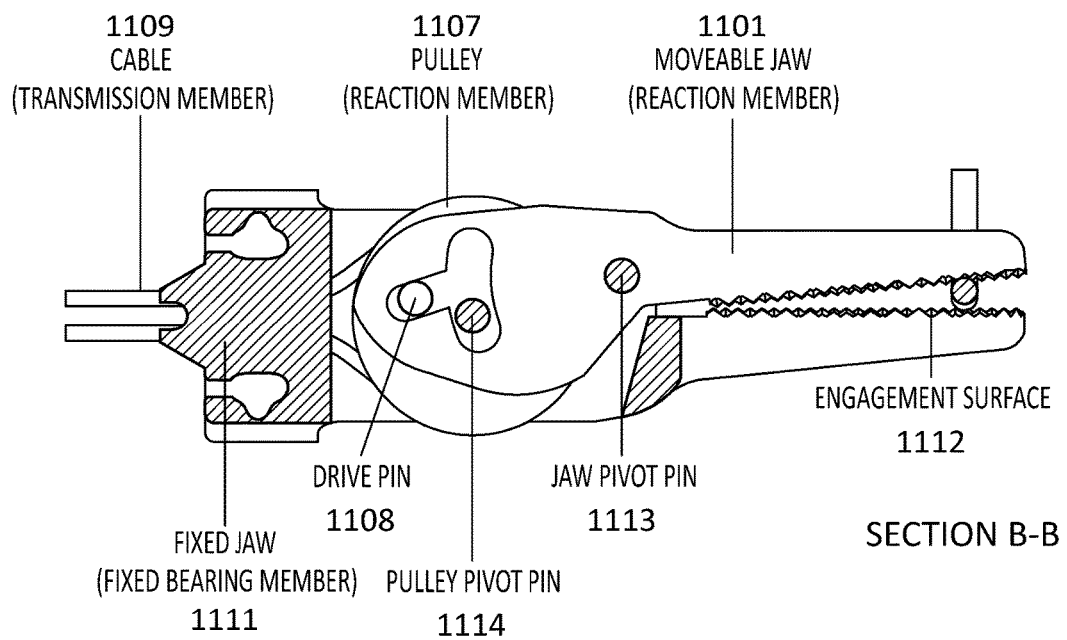
Figure 13:
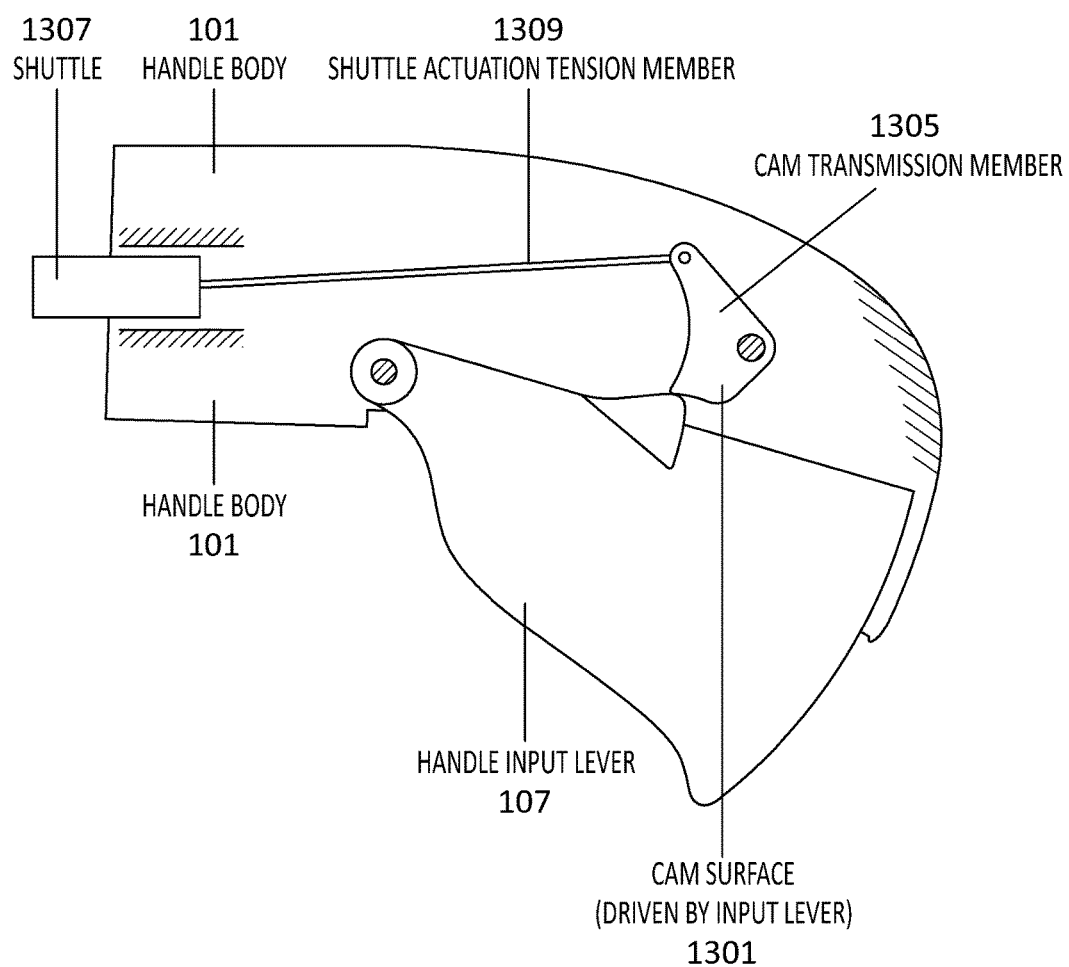
FIG. 13 shows an input sub-system comprising a cam in the handle mechanism.
Figure 14:
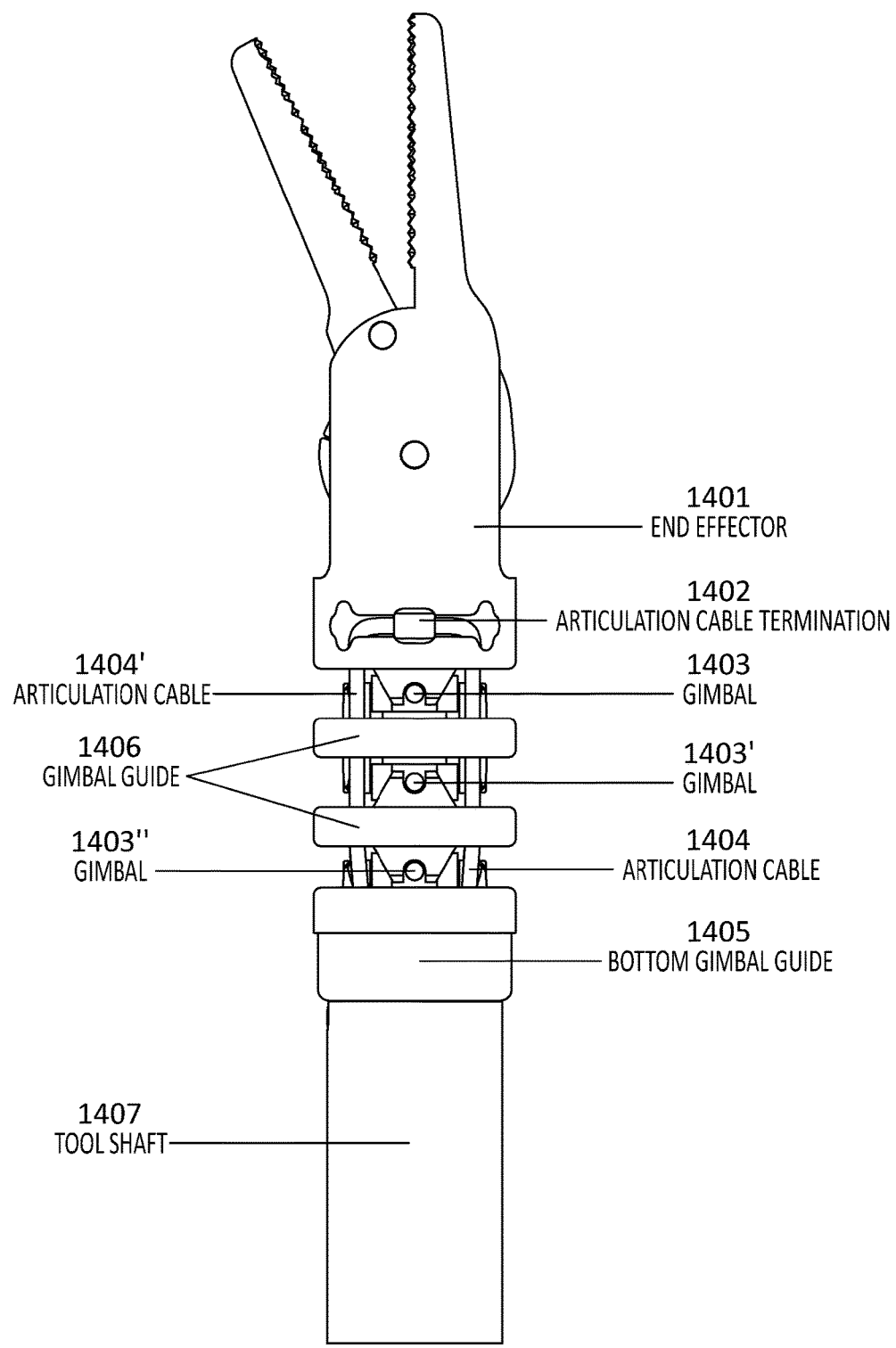
FIG. 14 shows an embodiment of an end-effector assembly including an output articulation joint (including gimbals 1403, 1403', 1403", gimbal guides 1406, articulation cables 1404, 1404', and bottom gimbal guide 1405) and including an end-effector 1401, articulation cable termination 1402, and tool shaft 1407.
Figure 15:
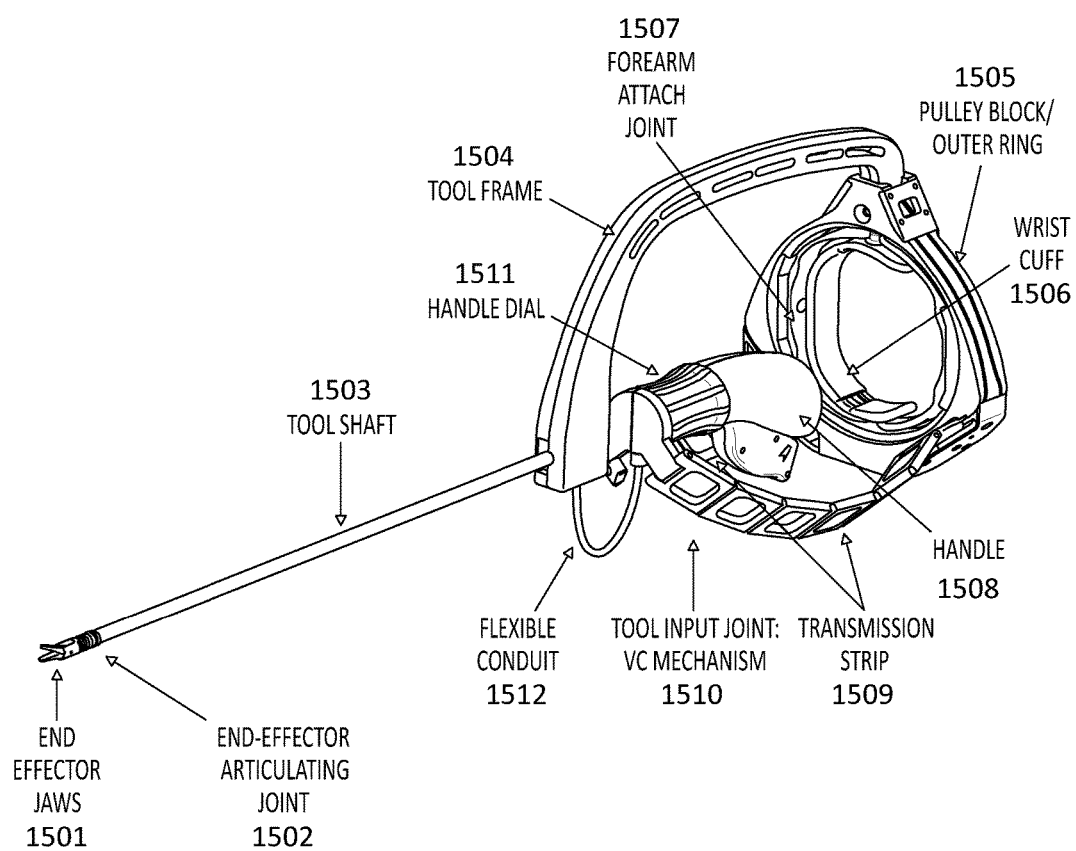
FIG. 15 shows an embodiment of a minimally invasive surgical device that incorporates a jaw closure transmission system as described here. The device includes end-effector jaws 1501, endeffector articulating joint 1502, tool shaft 1503, tool frame 1504 (including outer ring 1505), wrist cuff 1506, forearm attach joint 1507, handle 1508, handle dial 1511, transmission strip(s) 1509, tool input joint 1510 and flexible conduit 1512.
Figure 16:
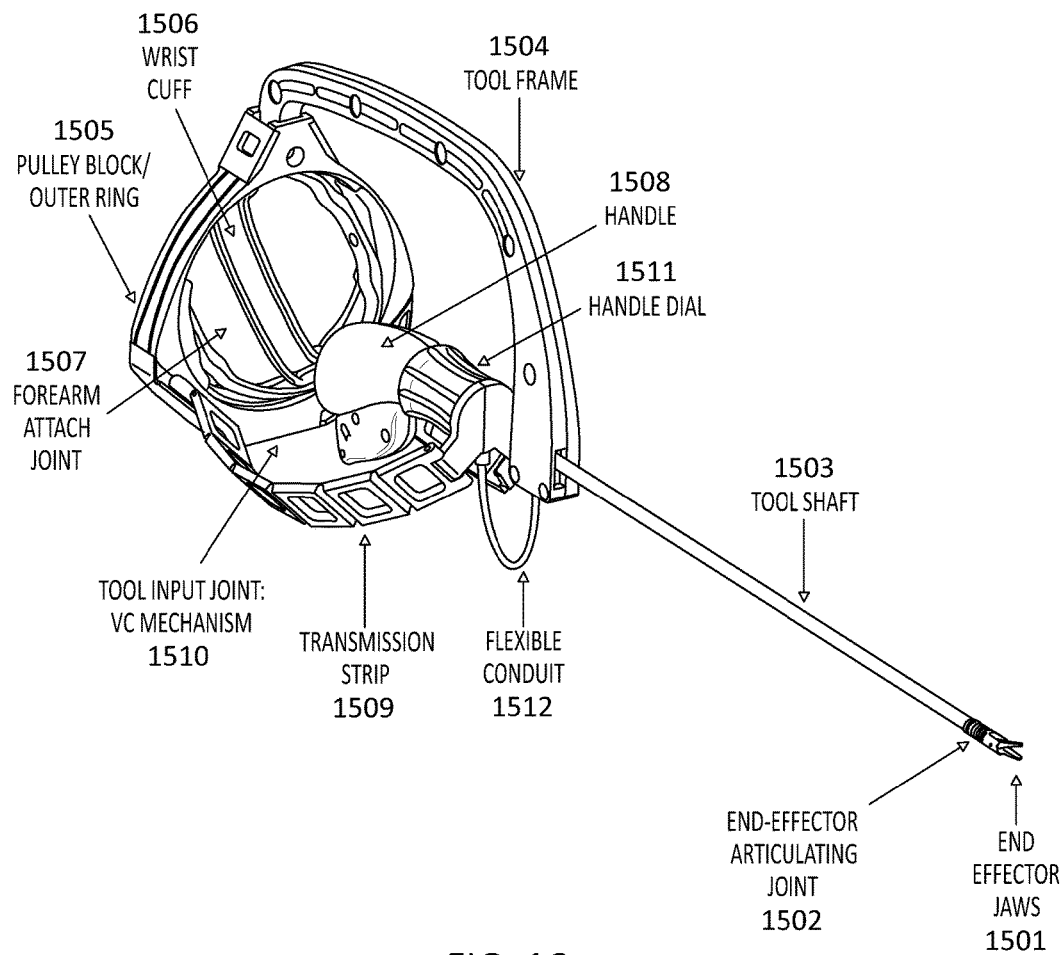
FIG. 16 shows an embodiment of a minimally invasive surgical device that incorporates a jaw closure transmission system as described here.

FIG. 8 graph 1 shows the handle output; the profile of this curve is achieved through the geometry of the handle mechanism. This graph indirectly shows the mechanical advantage and the transmission ratio of the handle mechanism. This profile is extremely important as it is a non-constant mechanical advantage which consists of a low mechanical advantage at the beginning of the input stroke and then increases the mechanical advantage towards the end of the stroke. Due to ergonomic reasons (or limits), the limit of input displacement and force at the handle varies throughout the lever stroke (through the range of angular displacement). A varying mechanical advantage in the system means that stroke A can have a completely different transmission ratio than in stroke B. During stroke A, the jaws are freely rotating in space, and therefore a high transmission ratio and low mechanical advantage can be implemented into the design during this phase which enables the jaws to achieve a wide opening angle. While in stroke B, when the jaws reach a hard stop, a higher mechanical advantage is desired such that a large clamping load at the output can ergonomically be applied from the input. The system transmission ratio comes from two sources, the handle mechanism and the jaw mechanism. The jaw mechanism which is seen in FIG. 8 graph 2, has a similar mechanical advantage and transmission ratio curve as the handle mechanism, a low mechanical advantage to start, and then a high mechanical advantage to end the stroke. However, the jaw mechanism has a different stroke than the input mechanism. The entirety of the jaw mechanism stroke is contained within stroke A, because the transition between stroke A and stroke B happens when the jaws reach a hard stop and the mechanism thereon remains fixed providing a constant mechanical advantage for the rest of the input stroke. The profile of the system's net mechanical advantage curve is seen in FIG. 9. This profile allows the user to apply a large clamping load with very little effort at the handle while still achieving a large jaw opening angle.

Graph 3 in FIG. 8 shows the performance of the compliant transmission member (cable). Since there is no force build up in stroke A, the cable does not stretch; however in stroke B, the cable is stretched because the jaw mechanism is fixed at the distal end while the input handle mechanism is still able to produce more cable displacement as the handle input lever reaches a full displacement (full stroke). A system with a much stiffer transmission member, such a steel rod or a flexible control wire, will not perform in this manner, as displacement at the input handle would be really hard to generate because the forces would directly relate to the clamping forces on the needle. A compliant transmission member allows for a soft buildup of force at the handle over a displacement to generate the closure force required. Cable tension is shown in graph 4. During stroke A the force felt at the handle input is the handle return spring which is shown in FIG. 8 to have a linear spring constant, K. As the stroke transitions to stroke B, the handle force is now the sum of the handle return spring and then tension in the cable, the more compliant the transmission member the less drastic the increase of input force is at the stroke A to B transition. As shown in graph 5, as the handle input lever achieves full stroke, the needle clamping force increases greatly based on the compliance of the cable and the amount of handle lever displacement left in stroke B. A transmission member that is too compliant would mean inadequate clamping load while a transmission member that is too stiff would require a ratcheting system and could damage the needle. As shown in graph 6 of FIG. 8, even as the needle clamping force increases, the handle lever input force doesn't increase as much due to the increasing high mechanical advantage of the handle mechanism and the fixed mechanical advantage of the jaw mechanism. This gradual increase in handle force while achieving optimal jaw closure eliminates the need of the multiple ratchet system that is required on needle drivers with a really stiff transmission member.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be conjointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a subset of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A medical device having a jaw assembly actuated by a transmission cable having a finite stiffness in an axial transmission direction wherein the transmission cable has a lower stiffness in bending relative to its stiffness in the axial transmission direction, the device comprising:
an elongate transmission guide, wherein the transmission cable is routed through the transmission guide;
a handle assembly at a proximal end of the elongate transmission guide, the handle assembly comprising a handle body, an input lever, a handle output coupled to the transmission cable, and a handle mechanism coupling the input lever to the handle output, wherein the handle mechanism has an input stroke consisting of a full closure displacement of the input lever relative to the handle body, further wherein the input stroke is divided into a first part and a second part, wherein the first part corresponds to a full closure of the jaw assembly with a displacement of 30% to 70% of the full closure displacement of the input lever and the second part corresponds to the remaining displacement of the input lever; and
wherein the jaw assembly is distal to the elongate transmission guide, the jaw assembly having a first jaw, a second jaw, a jaw input coupled to the transmission cable, and a jaw mechanism coupling the jaw input to the second jaw, wherein the jaw mechanism has an open configuration when the first and second jaws are fully open relative to each other and a closed configuration when the first and second jaws are fully closed; further wherein the displacement of the input lever relative to the handle body corresponding to the first part of the input stroke actuates the handle output which in turn actuates the jaw input via the transmission cable, which in turn closes the first and second jaws until the first and second jaws reach a hard stop, and thereafter the displacement of the input lever relative to the handle body corresponding to the second part of the input stroke stretches the transmission cable, wherein a resulting tension in the transmission cable is amplified by the jaw mechanism to a holding force between the first and second jaws.

2. The device of claim 1, wherein the handle mechanism comprises a linkage or a cam.

3. The device of claim 1, wherein the handle mechanism comprises a six-bar linkage.

4. The device of claim 1, wherein the elongate transmission guide comprises a flexible conduit or elongate shaft or both.

5. The device of claim 1, wherein the transmission cable has a stiffness in the axial transmission direction of less than 650 pounds per inch.

6. The device of claim 1, wherein handle mechanism is configured to provide a first mechanical advantage during the first part of the input stroke and a second mechanical advantage that is greater than the first mechanical advantage during the second part of the input stroke.

7. The device of claim 1, wherein the handle output comprises one or more of: a shuttle, a push rod, or a pull rod.

8. The device of claim 1, further comprising a jaw base to which either or both the first and second jaws are pivotally coupled.

9. The device of claim 1, wherein the jaw input comprises a jaw pulley, and the jaw mechanism comprises a cam surface between the jaw pulley and the second jaw.

10. The device of claim 1, further comprising a releasable latching mechanism configured to hold the input lever locked in a closed position at the end of the input stroke.

11. A medical device having a distal jaw assembly actuated by a transmission cable having a finite stiffness in an axial transmission direction wherein the transmission cable has a lower stiffness in bending relative to its stiffness in the axial transmission direction, the device comprising:
 a tool frame comprising an elongate shaft and a forearm attachment region at a proximal end of the tool frame configured to couple with an arm attachment cuff;
 a handle assembly, the handle assembly comprising a handle shell configured to be gripped in a user's palm and an input lever on the handle shell, wherein the handle shell encloses a handle linkage coupling the input lever to the transmission cable through a handle output, further wherein the handle assembly has an input stroke consisting of a full closure displacement of the input lever from an undisplaced configuration to a fully displaced configuration, further wherein the input lever transitions from a first part of the input stroke to a second part of the input stroke to fully close the jaw assembly when the input lever is displaced from an undisplaced configuration to between 30% and 70% of the full closure displacement of the input lever;
 an input joint between the handle assembly and the tool frame configured to encode motion of the handle assembly about a pitch axis of rotation relative to the tool frame for transmission to an articulating output joint, and further configured to encode motion of the handle assembly about a yaw axis of rotation relative to the tool frame for transmission to the articulating output joint, wherein the pitch axis of rotation and the yaw axis of rotation intersect in a center of rotation;
 wherein the jaw assembly is coupled to the distal end of an elongate tool shaft by the articulating output joint, the jaw assembly having a first jaw, a jaw pulley pivotally coupled to the first jaw and further coupled to the transmission cable, a second jaw pivotally coupled to the first jaw, and a cam surface that translates motion of the jaw pulley to a motion of the second jaw relative to the first jaw, wherein the jaw assembly has an output stroke that extends from an open configuration when the first and second jaws are fully open to a closed configuration when the first and second jaws are fully closed;
 wherein a displacement of the input lever relative to the handle shell corresponding to the first part of the input stroke actuates the handle output which in turn actuates the jaw input via the transmission cable, which in turn closes the first and second jaws until the first and second jaws reach the hard stop, and thereafter the displacement of the input lever relative to the handle shell corresponding to the second part of the input stroke stretches the transmission cable, wherein a resulting tension in the transmission cable is converted by the jaw assembly to a holding force between the first and second jaws; and
 a transmission guide extending between the handle assembly and the elongate shaft, wherein the transmission cable extends from the handle assembly, through the transmission guide to the jaw assembly.

12. A method of operating a medical device to close a jaw assembly of the medical device, wherein the medical device comprises an elongate transmission guide, a finite stiffness transmission cable within the transmission guide, wherein the transmission cable has a lower stiffness in bending relative to its stiffness in an axial transmission direction, and a handle assembly at a proximal end of the elongate transmission guide having an input lever and a handle mechanism coupling the input lever to the transmission cable, wherein the transmission cable is coupled to a jaw input of the jaw assembly, wherein the jaw assembly is distal to the elongate transmission guide, the method comprising:
 actuating the input lever to apply tension to the transmission cable during a first part of an input stroke of the handle assembly to close a first and second jaw of the jaw assembly from an open configuration until the first and second jaws reach a hard stop; and
 continuing to actuate the input lever during a second part of the input stroke after the first and second jaws have reached the hard stop and stretching the transmission cable;
 wherein the input stroke consists of a full displacement of the input lever of the handle assembly, and further wherein the handle assembly transitions from the first part of the input stroke to the second part of the input stroke when the handle is between 30% and 70% of the full displacement of the input lever.

13. The method of claim 12, further comprising applying a first mechanical advantage during the first part of the input stroke and applying a second mechanical advantage that is greater than the first mechanical advantage during the second part of the input stroke.

14. The method of claim 12, further comprising grasping an object between the first and second jaws, wherein the first and second jaws reach the hard stop when the object is secured between the first and second jaws.

15. The method of claim 12, further comprising locking the input lever in a fully closed position relative to a handle shell in the handle assembly.

16. The method of claim 12, further comprising releasing the input lever to transition the input lever from the second part of the input stroke to the first part of the input stroke, reducing tension on the transmission cable and reducing the stretch of the transmission cable before translating the transmission cable so that the first and second jaws open.

17. The method of claim 12, wherein actuating the input lever comprises squeezing the input lever.

* * * * *